United States Patent [19]

Kim et al.

[11] Patent Number: 5,512,596
[45] Date of Patent: Apr. 30, 1996

[54] AROMATIC COMPOUNDS

[75] Inventors: Choung U. Kim; Matthew A. Williams, both of Foster City, Calif.

[73] Assignee: Gilead Sciences, Inc., Foster City, Calif.

[21] Appl. No.: 300,607

[22] Filed: Sep. 2, 1994

[51] Int. Cl.⁶ ............................ A61K 31/19; C07C 63/06
[52] U.S. Cl. ........................ 514/568; 514/114; 514/570; 514/576; 514/619; 562/11; 562/58; 562/439; 562/560; 564/163
[58] Field of Search .................. 514/538, 565, 514/609, 637, 114, 568, 570, 576, 619; 560/22; 562/439, 11, 58, 104, 439, 560; 564/238, 239, 163

[56] References Cited

U.S. PATENT DOCUMENTS 5,302,720  4/1994  Gopalan .................................. 564/238

FOREIGN PATENT DOCUMENTS

0539204A1  10/1992  European Pat. Off. .
WO 91/16320  10/1991  WIPO .
WO 92/06691  4/1992  WIPO .

OTHER PUBLICATIONS

Luo et al., "Abstract of Presentation C52: Designed Non-Carbohydrate Inhibitors or Influenza Virus Neuraminidase And Accompanying Notes," *International Antiviral Conference, Nice, France, Jun. 10 (1994)*.

*Primary Examiner*—Yogendra N. Gupta
*Attorney, Agent, or Firm*—Mark L. Bosse

[57] ABSTRACT

A composition comprising a compound of the formula:

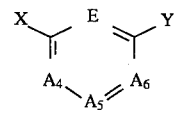

(18)

wherein:

X is H or OH;

Y is a group capable of hydrogen bonding to amino, guanidino, or imidazole function, or a group comprising an acidic hydrogen atom, a protected acidic group, or an anion;

E is N or $CR_1$, wherein $R_1$ is H, OH, CN, F, Cl, Br, or I;

$A_4$, $A_5$, and $A_6$ are each independently N, CH, $CR_{40}$ or CZ wherein $R_{40}$ is $R_{43}$, $OR_{43}$, $SR_{43}$, $S(O)R_{43}$, $S(O)_2R_{43}$, or $NR_{43}R_{44}$ wherein $R_{43}$ comprises an alkyl of 1 to 3 carbon atoms, an acyl of 2 to 3 carbon atoms, or an alkyl of 1 to 3 carbon atoms substituted with an acyl of 2 to 3 carbon atoms, and $R_{44}$ is H or an alkyl of 1 to 2 carbon atoms, and Z is a group capable of hydrogen bonding to carboxyl, or a group comprising a basic heteroatom, a protected basic heteroatom, or a cation.

12 Claims, No Drawings

AROMATIC COMPOUNDS

CROSS-REFERENCE TO RELATED APPLICATION

This application is related to U.S. patent application Ser. No. 08/116,417, filed Sep. 3, 1993 abandoned, which is incorporated in its entirety herein by reference. This application is also related to U.S. patent application having Attorney Docket Number 185.1, filed Sep. 2, 1994, which is incorporated in its entirety herein by reference.

BACKGROUND OF THE INVENTION

1. Field of the Invention

Neuraminidase (also known as sialidase, acylneuraminyl hydrolase, and EC 3.2.1.18) is an enzyme common among animals and a number of microorganisms. It is a glycohydrolase that cleaves terminal alpha-ketosidically linked sialic acids from glycoproteins, glycolipids and oligosaccharides. Many of the microorganisms containing neuraminidase are pathogenic to man and other animals including fowl, horses, swine and seals. These pathogenic organisms include influenza virus.

Neuraminidase has been implicated in the pathogenicity of influenza virus. It is thought to help the elution of newly synthesized virons from infected cells and assist in the movement of the virus (through its hydrolase activity) through the mucus of the respiratory tract.

Inhibition of glycolytic enzymes such as one of the neuraminidase are objects of the invention. Compositions capable of such inhibition are useful to limit the establishment and progression of infection by influenza virus and other neuraminidase utilizing organisms. Because neuraminidase cleaves sialic acid residues from a variety of biomolecules, compositions capable of such inhibition are also useful for inhibiting the cleavage of sialic acid residues from biomolecules. Accordingly, preparation of compositions capable of inhibiting neuraminidase is also an object of the invention.

An additional object is to provide compositions useful in preparing polymers and surfactant and for use in other industrial processes and articles.

2. Brief Description of Related Art

Itzstein, M. von; et al.; Nature 1993, 363(6428), 418–423, discloses the rational design of sialidase-based inhibitors of influenza virus replication.

Colman, P. M.; et al.; International Publication No. WO 92/06691 (Int. App. No. PCT/AU90/00501, publication date Apr. 30, 1992), discloses anti-viral compounds that bind neuraminidase.

SUMMARY OF THE INVENTION

One aspect of the invention is directed to a composition comprising a compound of the formula:

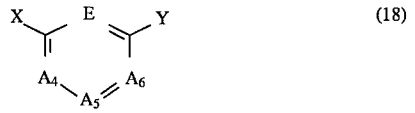 (18)

wherein X is H or OH; Y is a group capable of hydrogen bonding to amino, guanidino, or imidazole function, or a group comprising an acidic hydrogen atom, a protected acidic group, or an anion; E is N or $CR_1$, wherein $R_1$ is H, OH, CN, F, Cl, Br, or I; $A_4$, $A_5$, and $A_6$ are each independently N, CH, $CR_{40}$ or CZ wherein $R_{40}$ is $R_{43}$, $OR_{43}$, $SR_{43}$, $S(O)R_{43}$, $S(O)_2R_{43}$, or $NR_{43}R_{44}$ wherein $R_{43}$ comprises an alkyl of 1 to 3 carbon atoms, an acyl of 2 to 3 carbon atoms, or an alkyl of 1 to 3 carbon atoms substituted with an acyl of 2 to 3 carbon atoms, and $R_{44}$ is H or an alkyl of 1 to 2 carbon atoms, and Z is a group capable of hydrogen bonding to carboxyl, or a group comprising a basic heteroatom, a protected basic heteroatom, or a cation, with the proviso that one of $A_4$, $A_5$, and $A_6$ is CZ and the others are N, CH, or $CR_{40}$; or one of $A_4$, $A_5$, and $A_6$ is N, CH, or $CR_{40}$ and the remaining two are adjacent and one is CH or $CR_{40}$ and the other is CZ, and CH or $CR_{40}$ is taken together with CZ to form a 5 to 7 membered heterocyclic ring comprising Z; with the further proviso that when X is OH, then E is not $CR_1$ wherein $R_1$ is OH; with the further proviso that when E is CH, X is H, Y is $CO_2H$, $A_4$ is $N(H)C(O)CH_3$, and $A_6$ is CH, then $A_5$ is not $CNH_2$ or $CNO_2$; with the further proviso that when E is CH, X is OH, Y is $CO_2H$, $A_4$ is $N(H)C(O)CH_3$, and $A_6$ is CH, then $A_5$ is not $CNH_2$; and salts and solvates thereof.

Another aspect of the invention relates to a composition comprising a compound is of the formula:

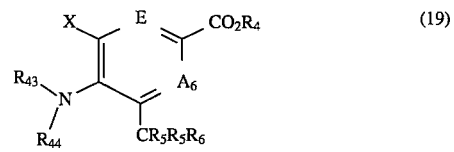 (19)

wherein $R_4$ is independently H or a group of 1 to 24 carbon atoms; $R_5$ are H, or or are taken together to form =NH; and $R_6$ comprises an amine, or a group having 1 to 12 carbon atoms and 1 to 3 amine groups.

Another aspect of the invention relates to the foregoing compositions comprising one or more pharmaceutically-acceptable carriers.

Another aspect of the invention relates to methods of inhibiting the activity of neuraminidase comprising the step of treating a sample suspected of containing neuraminidase with one or more of the foregoing compositions.

BRIEF DESCRIPTION OF THE DRAWINGS

FIGS. 1a and 1b depict exemplary aromatic carbocycles and heterocycles falling within structures (1) and (3), wherein $Q_1$, $Q_2$ and $Q_3$ represent the substitution sites for X, Y, and Z respectively.

FIGS. 2a–2c depict exemplary X groups, wherein $Q_1$ designates the FIGS. 1a and 1b carbocycle or heterocycle substitution sites.

FIG. 3 depicts exemplary Y groups, wherein $Q_2$ designates the FIGS. 1a and 1b carbocycle or heterocycle substitution sites.

FIGS. 4a–4c depict exemplary Z groups, wherein $Q_3$ designates the FIGS. 1a and 1b carbocycle or heterocycle substitution sites.

FIGS. 5a–b depict exemplary $R_{40}$ groups, wherein $Q_4$ designates the FIGS. 1a and 1b carbocycle or heterocycle substitution sites.

DETAILED DESCRIPTION

Compositions of the Invention

Typically, the compositions of the invention comprise compounds of the formulas:

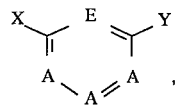 (1)

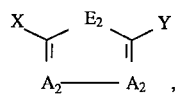 (3)

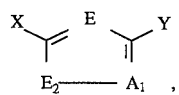 (15)

and

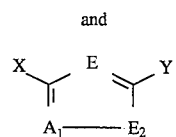 (16)

X is $R_{41}$, $OR_{41}$, $SR_{41}$, $S(O)R_{41}$, $S(O)_2R_{41}$, or $NR_{41}R_{42}$ wherein $R_{41}$ is H, OH, an alkyl group comprising 1 to 6 carbon atoms and 1 to 4 hydroxyl groups. The alkyl group is normal, branched, cyclic or a combination thereof. The hydroxyl groups are primary, secondary or tertiary. Typically X is H, OH, or a normal alkyl containing 3 to 5 carbon atoms and 2 to 3 hydroxyl groups. Ordinary X groups include, by way of example and not limitation, H, OH, ethanol, propanol, butanol, ethylene glycol, propylene glycol, and glycerol moieties having various configurations and stereochemistries. X ordinarily is H, OH, or a residue or radical of a naturally occuring carbohydrate such as glycerol, erythritol, threitol, adonitol, arabitol, and xylitol. $R_{42}$ is H, OH, alkyl of 1 to 3 carbon atoms, or comprises an amine. Exemplary X groups are listed in FIGS. 2a–2c.

Y comprises a group capable of hydrogen bonding to an amino, guanidino or imidazole function group. Ordinarily Y is capable of hydrogen bonding to the side chain of an arginine, lysine, or histidine amino acid residue within a polypeptide. Exemplary Y groups of this type include carboxylic acid and nitro functions, such as $—CO_2R_4$ as defined below.

Y may also comprise an acidic hydrogen atom, which, within the context of the invention, means a group having a hydrogen atom that can be removed by a base yielding an anion or its corresponding salt or solvate. The general principles of acidity and basicity of organic materials are well understood and will not be detailed, however, a description appears in Streitwieser, A.; and Heathcock, C. H.; "Introduction to Organic Chemistry, Second Edition" (Macmillan, New York, 1981), pages 60–64. Generally, acidic groups of the invention have pK values less than that of water, usually less than pK=10, typically less than pK=8, and frequently less than pK=6. Such groups include the common organic acids.

By way of example and not limitation, typical Y groups include acids of carbon, sulfur, phosphorous, and nitrogen, such groups include carboxylic ($—CO—_2$), alkyl sulfuric (alk-O—$SO_3H$), sulfonic (alk-$SO_3H$), sulfinic (alk-$SO_2H$), alkyl phosphoric (alk-O-$PO_3H_2$), phosphoric (—O—$PO_3H_2$), alkyl phosphonic (alk-$PO_3H_2$), phosphonic (—$PO_3H_2$), monoalkyl alkyl phosphonic (alk-P(O-alk)$O_2H$) and tetrazoles. Ordinarily Y is carboxy (—$CO_2H$), methylene carboxy (—$CH_2CO_2H$), phosphonate, methylene phosphonate (—$CH_2PO_3H_2$), sulfonate (—$SO_3H$), methylene sulfonate (—$CH_2SO_3H$), or tetrazole. Exemplary Y groups are shown in FIG. 3. The nomenclature of phosphorous compounds is described by Corbridge, D. E. C. "Phosphorus. An outline of its chemistry, Biochemistry and technology." (Elsevier, New York, 1985), Appendix II, pages 731–733, and sections cited therein.

Y may also be a protected acidic group, which, within the context of the invention means an acidic group as described above that has been protected by one of the groups common in the art. Such groups are described in detail in Greene, T. W., "Protective Groups in Organic Synthesis" (John Wiley & sons, New York, 1981). Such groups include by way of example and not limitation, esters, amides, hydrizides, and the like. In some embodiments, the protecting group will be cleavable under physiological conditions, more typically it will be cleavable in vivo, where the protecting group forms an ester or amide with an acid hydroxyl, including hydrolyzable esters or amides with naturally-occurring alcohols or amino acids respectively. Typical Y groups that are hydrolyzable under physiological conditions include esters and/or amides of the foregoing acid phosphorus, sulfur and carboxyl groups, in particular esters with groups selected from aryl (especially phenyl), lower alkoxy-substituted aryl (especially O-ethoxyphenyl) or the alkylacyloxyalkyl groups of U.S. Pat. No. 4,968,788, or amides formed with a naturally-occurring amines such as one of the naturally occurring amino acids or a polypeptide. Each one or more of the acid hydroxyls are esterified or amidated. The substituent esters or amines optionally are the same, or they may be different. Thus, where Y contains $R_4$, optionally $R_4$ has the structure $CH_2O(CO)R_{37}$ or $CH_2(CO)OR_{38}$ wherein $R_{37}$ and $R_{38}$ are alkyl, aryl, or alkylaryl groups. Frequently $R_{37}$ and $R_{38}$ are bulky groups such as branched alkyl, ortho-substituted aryl, meta-substituted aryl, or combinations thereof, including normal, secondary, iso- and tertiary alkyls of 1–6 carbon atoms.

In some embodiments Y is taken together with Z to form an intramolecularly protected Y group. For example, when Y is a carboxylic acid function (e.g. a —$CO_2H$ group) and Z comprises an amine function (e.g. a —$(CH_2)_m$—$NH_2$ group, wherein m is 1 to 4), the intramolecular cyclic amide is a intramolecularly protected Y and Z group.

E is N or $CR_1$, wherein $R_1$ is H, OH, CN, F, Cl, Br, or I.

$E_2$ is O, NH, or S.

A is independently N, CH, $CR_{40}$ or CZ, provided that one A is CZ and the others are N, CH, or $CR_{40}$; or one A is N, CH, or $CR_{40}$ and the remaining two are adjacent to one another and one is CH or $CR_{40}$ and the other is CZ, and CH or $CR_{40}$ is taken together with CZ to form a 5 to 7 membered heterocyclic ring comprising Z $A_1$ is CZ.

$A_2$ is independently N, CH, or $CR_{40}$, provided that one $A_2$ is CZ and the other is N, CH, or $CR_{40}$; or one $A_2$ is CZ and the other is CH or $CR_{40}$, and CH or $CR_{40}$ is taken together with CZ to form a 5 to 7 membered heterocyclic ring comprising Z;

$R_{40}$ is $R_{43}$, $OR_{43}$, $SR_{43}$, $S(O)R_{43}$, $S(O)_2R_{43}$, or $NR_{43}R_{44}$ wherein $R_{43}$ comprises an alkyl of 1 to 3 carbon atoms, an acyl of 2 to 3 carbon atoms, or an alkyl of 1 to 3 carbon atoms substituted with an acyl of 2 to 3 carbon atoms, and $R_{44}$ is H or an alkyl of 1 to 2 carbon atoms.

Exemplary $R_{43}$ groups include by way of example and not limitation, methyl ($CH_3$, group .1 in FIG. 5a), ethyl (CH₃CH₂, group .2 in FIG. 5a), n-propyl (CH₃CH₂CH₂, group .3 in FIG. 5a), i-propyl ((CH₃)₂CH, group .4 in FIG. 5a), 2 carbon acyl (CH₃C(O), group .5 in FIG. 5a), 3 carbon acyl (CH₃CH₂C(O), group .6 in FIG. 5a), 1 carbon alkyl having a 2 carbon acyl (2-propanone-1-yl, CH₃C(O)CH₂, group .7 in FIG. 5a), 1 carbon alkyl having a 3 carbon acyl (2-butanone-1-yl, CH₃CH₂C(O)CH₂), 2 carbon alkyl having a 2 carbon acyl (e.g. 2-butanone-3-yl, CH₃C(O)CHCH₃ or 2-butanone-4-yl, CH₃C(O)CH₂CH₂), and the like. Ordinarily $R_{43}$ is a 2 or 3 carbon acyl.

$R_{43}$ is optionally substituted with one or more non-polar electron withdrawing groups. When $R_{43}$ is an Acyl of 2 to 3 carbon atoms, the substitution by the non-polar electron withdrawing group is typically on the carbon atom alpha to the acyl carbonyl carbon atom. Such groups are well known in the art and, by way of example and not limitation, they include halides (e.g. F, Cl, Br, or I), pseudo halides (e.g. CN), and atoms having electronegativities greater than hydrogen and being capable of forming covalent bonds to carbon wherein the bonds are stable under physiological conditions. Ordinary non-polar electron withdrawing groups are halides and in particular F. Exemplary $R_{43}$ groups having non-polar electronwithdrawing groups include mono-, di-, and trihalo- acyl groups of 2 to 3 carbon atom such as mono-, di-, and trifluoro- 2 carbon acyl.

Z comprises a group capable of hydrogen bonding to a carboxyl group. Ordinarily Z is capable of hydrogen bonding to the side chain of an aspartate or glutamate amino acid residue within a polypeptide. Z generally comprises a basic heteroatom, which, within the context of the invention means a heteroatom capable of protonation, typically by an acidic hydrogen having an acidity in the range described above for Y. The basic principals of basicity are described in Streitwieser and Heathcock (op. cit.). Generally, basic heteroatoms of the invention have pK values for the corresponding protonated form that are in the range of values described above for Y. Basic heteroatoms include the heteroatoms common in organic compounds which have an un-shared, non-bonding, n-type, or the like, electron pair. By way of example and not limitation, typical basic heteroatoms include the oxygen, nitrogen, and sulfur atoms of groups such as alcohols, amines, amidines, guanidines, sulfides, and the like, frequently, amines, amidines and guanidines. Ordinarily, Z is an amino alkyl (generally lower alkyl) group such as aminomethyl, aminoethyl or aminopropyl; an amidinoalkyl group such as amidinomethyl, amidinoethyl, or amidinopropyl; or a guanidinoalkyl group such as guanidinomethyl, guanidinoethyl, or guanidinopropyl. Z typically is —CR₅R₅R₆ a-(CH₂)ₘR₆ as defined below. A number of exemplary Z groups are shown in FIGS. 4a–4c.

Z optionally is a protected basic heteroatom, which, within the context of the invention means a basic heteroatom as described above that has been protected by one of the groups common in the art. Such groups are described in detail in Greene (op. cit.). Such groups include by way of example and not limitation, amides, carbamates, amino acetals, imines, enamines, N-alkyl or N-aryl phosphinyls, N-alkyl or N-aryl sulfenyls or sulfonyls, N-alkyl or N-aryl silyls, thioethers, thioesters, disulfides, sulfenyls, and the like. In some embodiments, the protecting group will be cleavable under physiological conditions, typically it will be cleavable in vivo where, for example, the basic heteroatom forms an amide with an organic acid or an amino acid such as a naturally occurring amino acid or a polypeptide.

One of Y and Z may alternatively be H. When Y or Z is H, X comprises an alkyl of 3 to 6 carbon atoms having 2 to 4 hydroxyls One embodiment of the invention is a compound of the formula:

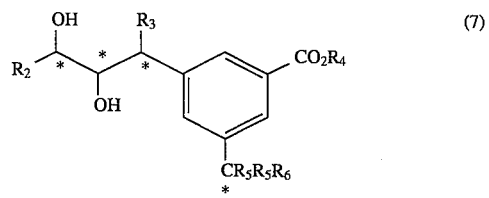

(7)

Wherein $R_2$ is H or an alkyl group having 1 to 3 carbon atoms and 0 to 2 hydroxyls; $R_3$ is H, or hydroxyl; $R_4$ is H, or forms a hydrolyzable ester or amide with —CO₂—; $R_5$ are H, or are taken together to form =NH; $R_6$ is —NH₂, or comprises a group having 1 to 12 carbon atoms and 1 to 3 amine groups.

Ordinarily, $R_2$ is H; $R_3$ is H or OH; $R_4$ is H; and $R_5$ are taken together to form =NH and $R_6$ is NH2; or $R_5$ are H and $R_6$ is amino substituted $C_1$–$C_{12}$ (ordinarily $C_1$–$C_6$) alkyl such as aminomethyl, aminoethyl or aminopropyl.

Another embodiment of the invention is a compound of the formula:

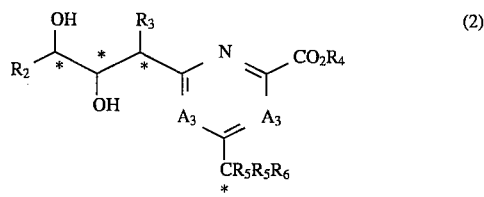

(2)

Wherein $R_2$, $R_3$, $R_4$, $R_5$ and $R_6$ are defined above $A_3$ is independently N, CH or $CR_{40}$ and $R_{40}$ is defined above.

Another embodiment of the invention is a compound of the formula:

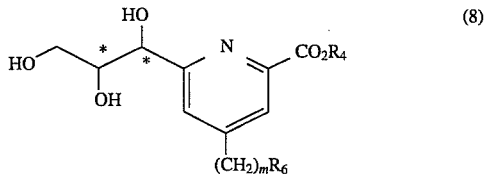

(8)

Wherein $R_4$ and $R_6$ are defined above, and m is 1 to 4. Ordinarily, m is 1 or 2.

Another embodiment of the invention is a compound of the formula:

TABLE 1

| Exemplary Enumerated Compounds | | | | |
|---|---|---|---|---|
| 17.43.1.1.5 | 17.43.1.1.13 | 17.43.1.1.18 | 17.43.1.1.22 | 17.43.1.1.25 |
| 17.43.1.2.5 | 17.43.1.2.13 | 17.43.1.2.18 | 17.43.1.2.22 | 17.43.1.2.25 |
| 17.43.1.5.5 | 17.43.1.5.13 | 17.43.1.5.18 | 17.43.1.5.22 | 17.43.1.5.25 |
| 17.43.1.7.5 | 17.43.1.7.13 | 17.43.1.7.18 | 17.43.1.7.22 | 17.43.1.7.25 |

TABLE 1-continued

Exemplary Enumerated Compounds

| | | | | |
|---|---|---|---|---|
| 17.43.1.46.5 | 17.43.1.46.13 | 17.43.1.46.18 | 17.43.1.46.22 | 17.43.1.46.25 |
| 17.43.1.47.5 | 17.43.1.47.13 | 17.43.1.47.18 | 17.43.1.47.22 | 17.43.1.47.25 |
| 17.43.2.1.5 | 17.43.2.1.13 | 17.43.2.1.18 | 17.43.2.1.22 | 17.43.2.1.25 |
| 17.43.2.2.5 | 17.43.2.2.13 | 17.43.2.2.18 | 17.43.2.2.22 | 17.43.2.2.25 |
| 17.43.2.5.5 | 17.43.2.5.13 | 17.43.2.5.18 | 17.43.2.5.22 | 17.43.2.5.25 |
| 17.43.2.7.5 | 17.43.2.7.13 | 17.43.2.7.18 | 17.43.2.7.22 | 17.43.2.7.25 |
| 17.43.2.46.5 | 17.43.2.46.13 | 17.43.2.46.18 | 17.43.2.46.22 | 17.43.2.46.25 |
| 17.43.2.47.5 | 17.43.2.47.13 | 17.43.2.47.18 | 17.43.2.47.22 | 17.43.2.47.25 |
| 17.43.6.1.5 | 17.43.6.1.13 | 17.43.6.1.18 | 17.43.6.1.22 | 17.43.6.1.25 |
| 17.43.6.2.5 | 17.43.6.2.13 | 17.43.6.2.18 | 17.43.6.2.22 | 17.43.6.2.25 |
| 17.43.6.5.5 | 17.43.6.5.13 | 17.43.6.5.18 | 17.43.6.5.22 | 17.43.6.5.25 |
| 17.43.6.7.5 | 17.43.6.7.13 | 17.43.6.7.18 | 17.43.6.7.22 | 17.43.6.7.25 |
| 17.43.6.46.5 | 17.43.6.46.13 | 17.43.6.46.18 | 17.43.6.46.22 | 17.43.6.46.25 |
| 17.43.6.47.5 | 17.43.6.47.13 | 17.43.6.47.18 | 17.43.6.47.22 | 17.43.6.47.25 |
| 17.43.7.1.5 | 17.43.7.1.13 | 17.43.7.1.18 | 17.43.7.1.22 | 17.43.7.1.25 |
| 17.43.7.2.5 | 17.43.7.2.13 | 17.43.7.2.18 | 17.43.7.2.22 | 17.43.7.2.25 |
| 17.43.7.5.5 | 17.43.7.5.13 | 17.43.7.5.18 | 17.43.7.5.22 | 17.43.7.5.25 |
| 17.43.7.7.5 | 17.43.7.7.13 | 17.43.7.7.18 | 17.43.7.7.22 | 17.43.7.7.25 |
| 17.43.7.46.5 | 17.43.7.46.13 | 17.43.7.46.18 | 17.43.7.46.22 | 17.43.7.46.25 |
| 17.43.7.47.5 | 17.43.7.47.13 | 17.43.7.47.18 | 17.43.7.47.22 | 17.43.7.47.25 |
| 17.43.8.1.5 | 17.43.8.1.13 | 17.43.8.1.18 | 17.43.8.1.22 | 17.43.8.1.25 |
| 17.43.8.2.5 | 17.43.8.2.13 | 17.43.8.2.18 | 17.43.8.2.22 | 17.43.8.2.25 |
| 17.43.8.5.5 | 17.43.8.5.13 | 17.43.8.5.18 | 17.43.8.5.22 | 17.43.8.5.25 |
| 17.43.8.7.5 | 17.43.8.7.13 | 17.43.8.7.18 | 17.43.8.7.22 | 17.43.8.7.25 |
| 17.43.8.46.5 | 17.43.8.46.13 | 17.43.8.46.18 | 17.43.8.46.22 | 17.43.8.46.25 |
| 17.43.8.47.5 | 17.43.8.47.13 | 17.43.8.47.18 | 17.43.8.47.22 | 17.43.8.47.25 |
| 17.43.9.1.5 | 17.43.9.1.13 | 17.43.9.1.18 | 17.43.9.1.22 | 17.43.9.1.25 |
| 17.43.9.2.5 | 17.43.9.2.13 | 17.43.9.2.18 | 17.43.9.2.22 | 17.43.9.2.25 |
| 17.43.9.5.5 | 17.43.9.5.13 | 17.43.9.5.18 | 17.43.9.5.22 | 17.43.9.5.25 |
| 17.43.9.7.5 | 17.43.9.7.13 | 17.43.9.7.18 | 17.43.9.7.22 | 17.43.9.7.25 |
| 17.43.9.46.5 | 17.43.9.46.13 | 17.43.9.46.18 | 17.43.9.46.22 | 17.43.9.46.25 |
| 17.43.9.47.5 | 17.43.9.47.13 | 17.43.9.47.18 | 17.43.9.47.22 | 17.43.9.47.25 |
| 17.43.10.1.5 | 17.43.10.1.13 | 17.43.10.1.18 | 17.43.10.1.22 | 17.43.10.1.25 |
| 17.43.10.2.5 | 17.43.10.2.13 | 17.43.10.2.18 | 17.43.10.2.22 | 17.43.10.2.25 |
| 17.43.10.5.5 | 17.43.10.5.13 | 17.43.10.5.18 | 17.43.10.5.22 | 17.43.10.5.25 |
| 17.43.10.7.5 | 17.43.10.7.13 | 17.43.10.7.18 | 17.43.10.7.22 | 17.43.10.7.25 |
| 17.43.10.46.5 | 17.43.10.46.13 | 17.43.10.46.18 | 17.43.10.46.22 | 17.43.10.46.25 |
| 17.43.10.47.5 | 17.43.10.47.13 | 17.43.10.47.18 | 17.43.10.47.22 | 17.43.10.47.25 |
| 17.44.1.1.5 | 17.44.1.1.13 | 17.44.1.1.18 | 17.44.1.1.22 | 17.44.1.1.25 |
| 17.44.1.2.5 | 17.44.1.2.13 | 17.44.1.2.18 | 17.44.1.2.22 | 17.44.1.2.25 |
| 17.44.1.5.5 | 17.44.1.5.13 | 17.44.1.5.18 | 17.44.1.5.22 | 17.44.1.5.25 |
| 17.44.1.7.5 | 17.44.1.7.13 | 17.44.1.7.18 | 17.44.1.7.22 | 17.44.1.7.25 |
| 17.44.1.46.5 | 17.44.1.46.13 | 17.44.1.46.18 | 17.44.1.46.22 | 17.44.1.46.25 |
| 17.44.1.47.5 | 17.44.1.47.13 | 17.44.1.47.18 | 17.44.1.47.22 | 17.44.1.47.25 |
| 17.44.2.1.5 | 17.44.2.1.13 | 17.44.2.1.18 | 17.44.2.1.22 | 17.44.2.1.25 |
| 17.44.2.2.5 | 17.44.2.2.13 | 17.44.2.2.18 | 17.44.2.2.22 | 17.44.2.2.25 |
| 17.44.2.5.5 | 17.44.2.5.13 | 17.44.2.5.18 | 17.44.2.5.22 | 17.44.2.5.25 |
| 17.44.2.7.5 | 17.44.2.7.13 | 17.44.2.7.18 | 17.44.2.7.22 | 17.44.2.7.25 |
| 17.44.2.46.5 | 17.44.2.46.13 | 17.44.2.46.18 | 17.44.2.46.22 | 17.44.2.46.25 |
| 17.44.2.47.5 | 17.44.2.47.13 | 17.44.2.47.18 | 17.44.2.47.22 | 17.44.2.47.25 |
| 17.44.6.1.5 | 17.44.6.1.13 | 17.44.6.1.18 | 17.44.6.1.22 | 17.44.6.1.25 |
| 17.44.6.2.5 | 17.44.6.2.13 | 17.44.6.2.18 | 17.44.6.2.22 | 17.44.6.2.25 |
| 17.44.6.5.5 | 17.44.6.5.13 | 17.44.6.5.18 | 17.44.6.5.22 | 17.44.6.5.25 |
| 17.44.6.7.5 | 17.44.6.7.13 | 17.44.6.7.18 | 17.44.6.7.22 | 17.44.6.7.25 |
| 17.44.6.46.5 | 17.44.6.46.13 | 17.44.6.46.18 | 17.44.6.46.22 | 17.44.6.46.25 |
| 17.44.6.47.5 | 17.44.6.47.13 | 17.44.6.47.18 | 17.44.6.47.22 | 17.44.6.47.25 |
| 17.44.7.1.5 | 17.44.7.1.13 | 17.44.7.1.18 | 17.44.7.1.22 | 17.44.7.1.25 |
| 17.44.7.2.5 | 17.44.7.2.13 | 17.44.7.2.18 | 17.44.7.2.22 | 17.44.7.2.25 |
| 17.44.7.5.5 | 17.44.7.5.13 | 17.44.7.5.18 | 17.44.7.5.22 | 17.44.7.5.25 |
| 17.44.7.7.5 | 17.44.7.7.13 | 17.44.7.7.18 | 17.44.7.7.22 | 17.44.7.7.25 |
| 17.44.7.46.5 | 17.44.7.46.13 | 17.44.7.46.18 | 17.44.7.46.22 | 17.44.7.46.25 |
| 17.44.7.47.5 | 17.44.7.47.13 | 17.44.7.47.18 | 17.44.7.47.22 | 17.44.7.47.25 |
| 17.44.8.1.5 | 17.44.8.1.13 | 17.44.8.1.18 | 17.44.8.1.22 | 17.44.8.1.25 |
| 17.44.8.2.5 | 17.44.8.2.13 | 17.44.8.2.18 | 17.44.8.2.22 | 17.44.8.2.25 |
| 17.44.8.5.5 | 17.44.8.5.13 | 17.44.8.5.18 | 17.44.8.5.22 | 17.44.8.5.25 |
| 17.44.8.7.5 | 17.44.8.7.13 | 17.44.8.7.18 | 17.44.8.7.22 | 17.44.8.7.25 |
| 17.44.8.46.5 | 17.44.8.46.13 | 17.44.8.46.18 | 17.44.8.46.22 | 17.44.8.46.25 |
| 17.44.8.47.5 | 17.44.8.47.13 | 17.44.8.47.18 | 17.44.8.47.22 | 17.44.8.47.25 |
| 17.44.9.1.5 | 17.44.9.1.13 | 17.44.9.1.18 | 17.44.9.1.22 | 17.44.9.1.25 |
| 17.44.9.2.5 | 17.44.9.2.13 | 17.44.9.2.18 | 17.44.9.2.22 | 17.44.9.2.25 |
| 17.44.9.5.5 | 17.44.9.5.13 | 17.44.9.5.18 | 17.44.9.5.22 | 17.44.9.5.25 |
| 17.44.9.7.5 | 17.44.9.7.13 | 17.44.9.7.18 | 17.44.9.7.22 | 17.44.9.7.25 |
| 17.44.9.46.5 | 17.44.9.46.13 | 17.44.9.46.18 | 17.44.9.46.22 | 17.44.9.46.25 |
| 17.44.9.47.5 | 17.44.9.47.13 | 17.44.9.47.18 | 17.44.9.47.22 | 17.44.9.47.25 |
| 17.44.10.1.5 | 17.44.10.1.13 | 17.44.10.1.18 | 17.44.10.1.22 | 17.44.10.1.25 |
| 17.44.10.2.5 | 17.44.10.2.13 | 17.44.10.2.18 | 17.44.10.2.22 | 17.44.10.2.25 |
| 17.44.10.5.5 | 17.44.10.5.13 | 17.44.10.5.18 | 17.44.10.5.22 | 17.44.10.5.25 |

TABLE 1-continued

Exemplary Enumerated Compounds

| | | | | |
|---|---|---|---|---|
| 17.44.10.7.5 | 17.44.10.7.13 | 17.44.10.7.18 | 17.44.10.7.22 | 17.44.10.7.25 |
| 17.44.10.46.5 | 17.44.10.46.13 | 17.44.10.46.18 | 17.44.10.46.22 | 17.44.10.46.25 |
| 17.44.10.47.5 | 17.44.10.47.13 | 17.44.10.47.18 | 17.44.10.47.22 | 17.44.10.47.25 |
| 18.43.1.1.5 | 18.43.1.1.13 | 18.43.1.1.18 | 18.43.1.1.22 | 18.43.1.1.25 |
| 18.43.1.2.5 | 18.43.1.2.13 | 18.43.1.2.18 | 18.43.1.2.22 | 18.43.1.2.25 |
| 18.43.1.5.5 | 18.43.1.5.13 | 18.43.1.5.18 | 18.43.1.5.22 | 18.43.1.5.25 |
| 18.43.1.7.5 | 18.43.1.7.13 | 18.43.1.7.18 | 18.43.1.7.22 | 18.43.1.7.25 |
| 18.43.1.46.5 | 18.43.1.46.13 | 18.43.1.46.18 | 18.43.1.46.22 | 18.43.1.46.25 |
| 18.43.1.47.5 | 18.43.1.47.13 | 18.43.1.47.18 | 18.43.1.47.22 | 18.43.1.47.25 |
| 18.43.2.1.5 | 18.43.2.1.13 | 18.43.2.1.18 | 18.43.2.1.22 | 18.43.2.1.25 |
| 18.43.2.2.5 | 18.43.2.2.13 | 18.43.2.2.18 | 18.43.2.2.22 | 18.43.2.2.25 |
| 18.43.2.5.5 | 18.43.2.5.13 | 18.43.2.5.18 | 18.43.2.5.22 | 18.43.2.5.25 |
| 18.43.2.7.5 | 18.43.2.7.13 | 18.43.2.7.18 | 18.43.2.7.22 | 18.43.2.7.25 |
| 18.43.2.46.5 | 18.43.2.46.13 | 18.43.2.46.18 | 18.43.2.46.22 | 18.43.2.46.25 |
| 18.43.2.47.5 | 18.43.2.47.13 | 18.43.2.47.18 | 18.43.2.47.22 | 18.43.2.47.25 |
| 18.43.6.1.5 | 18.43.6.1.13 | 18.43.6.1.18 | 18.43.6.1.22 | 18.43.6.1.25 |
| 18.43.6.2.5 | 18.43.6.2.13 | 18.43.6.2.18 | 18.43.6.2.22 | 18.43.6.2.25 |
| 18.43.6.5.5 | 18.43.6.5.13 | 18.43.6.5.18 | 18.43.6.5.22 | 18.43.6.5.25 |
| 18.43.6.7.5 | 18.43.6.7.13 | 18.43.6.7.18 | 18.43.6.7.22 | 18.43.6.7.25 |
| 18.43.6.46.5 | 18.43.6.46.13 | 18.43.6.46.18 | 18.43.6.46.22 | 18.43.6.46.25 |
| 18.43.6.47.5 | 18.43.6.47.13 | 18.43.6.47.18 | 18.43.6.47.22 | 18.43.6.47.25 |
| 18.43.7.1.5 | 18.43.7.1.13 | 18.43.7.1.18 | 18.43.7.1.22 | 18.43.7.1.25 |
| 18.43.7.2.5 | 18.43.7.2.13 | 18.43.7.2.18 | 18.43.7.2.22 | 18.43.7.2.25 |
| 18.43.7.5.5 | 18.43.7.5.13 | 18.43.7.5.18 | 18.43.7.5.22 | 18.43.7.5.25 |
| 18.43.7.7.5 | 18.43.7.7.13 | 18.43.7.7.18 | 18.43.7.7.22 | 18.43.7.7.25 |
| 18.43.7.46.5 | 18.43.7.46.13 | 18.43.7.46.18 | 18.43.7.46.22 | 18.43.7.46.25 |
| 18.43.7.47.5 | 18.43.7.47.13 | 18.43.7.47.18 | 18.43.7.47.22 | 18.43.7.47.25 |
| 18.43.8.1.5 | 18.43.8.1.13 | 18.43.8.1.18 | 18.43.8.1.22 | 18.43.8.1.25 |
| 18.43.8.2.5 | 18.43.8.2.13 | 18.43.8.2.18 | 18.43.8.2.22 | 18.43.8.2.25 |
| 18.43.8.5.5 | 18.43.8.5.13 | 18.43.8.5.18 | 18.43.8.5.22 | 18.43.8.5.25 |
| 18.43.8.7.5 | 18.43.8.7.13 | 18.43.8.7.18 | 18.43.8.7.22 | 18.43.8.7.25 |
| 18.43.8.46.5 | 18.43.8.46.13 | 18.43.8.46.18 | 18.43.8.46.22 | 18.43.8.46.25 |
| 18.43.8.47.5 | 18.43.8.47.13 | 18.43.8.47.18 | 18.43.8.47.22 | 18.43.8.47.25 |
| 18.43.9.1.5 | 18.43.9.1.13 | 18.43.9.1.18 | 18.43.9.1.22 | 18.43.9.1.25 |
| 18.43.9.2.5 | 18.43.9.2.13 | 18.43.9.2.18 | 18.43.9.2.22 | 18.43.9.2.25 |
| 18.43.9.5.5 | 18.43.9.5.13 | 18.43.9.5.18 | 18.43.9.5.22 | 18.43.9.5.25 |
| 18.43.9.7.5 | 18.43.9.7.13 | 18.43.9.7.18 | 18.43.9.7.22 | 18.43.9.7.25 |
| 18.43.9.46.5 | 18.43.9.46.13 | 18.43.9.46.18 | 18.43.9.46.22 | 18.43.9.46.25 |
| 18.43.9.47.5 | 18.43.9.47.13 | 18.43.9.47.18 | 18.43.9.47.22 | 18.43.9.47.25 |
| 18.43.10.1.5 | 18.43.10.1.13 | 18.43.10.1.18 | 18.43.10.1.22 | 18.43.10.1.25 |
| 18.43.10.2.5 | 18.43.10.2.13 | 18.43.10.2.18 | 18.43.10.2.22 | 18.43.10.2.25 |
| 18.43.10.5.5 | 18.43.10.5.13 | 18.43.10.5.18 | 18.43.10.5.22 | 18.43.10.5.25 |
| 18.43.10.7.5 | 18.43.10.7.13 | 18.43.10.7.18 | 18.43.10.7.22 | 18.43.10.7.25 |
| 18.43.10.46.5 | 18.43.10.46.13 | 18.43.10.46.18 | 18.43.10.46.22 | 18.43.10.46.25 |
| 18.43.10.47.5 | 18.43.10.47.13 | 18.43.10.47.18 | 18.43.10.47.22 | 18.43.10.47.25 |
| 18.44.1.1.5 | 18.44.1.1.13 | 18.44.1.1.18 | 18.44.1.1.22 | 18.44.1.1.25 |
| 18.44.1.2.5 | 18.44.1.2.13 | 18.44.1.2.18 | 18.44.1.2.22 | 18.44.1.2.25 |
| 18.44.1.5.5 | 18.44.1.5.13 | 18.44.1.5.18 | 18.44.1.5.22 | 18.44.1.5.25 |
| 18.44.1.7.5 | 18.44.1.7.13 | 18.44.1.7.18 | 18.44.1.7.22 | 18.44.1.7.25 |
| 18.44.1.46.5 | 18.44.1.46.13 | 18.44.1.46.18 | 18.44.1.46.22 | 18.44.1.46.25 |
| 18.44.1.47.5 | 18.44.1.47.13 | 18.44.1.47.18 | 18.44.1.47.22 | 18.44.1.47.25 |
| 18.44.2.1.5 | 18.44.2.1.13 | 18.44.2.1.18 | 18.44.2.1.22 | 18.44.2.1.25 |
| 18.44.2.2.5 | 18.44.2.2.13 | 18.44.2.2.18 | 18.44.2.2.22 | 18.44.2.2.25 |
| 18.44.2.5.5 | 18.44.2.5.13 | 18.44.2.5.18 | 18.44.2.5.22 | 18.44.2.5.25 |
| 18.44.2.7.5 | 18.44.2.7.13 | 18.44.2.7.18 | 18.44.2.7.22 | 18.44.2.7.25 |
| 18.44.2.46.5 | 18.44.2.46.13 | 18.44.2.46.18 | 18.44.2.46.22 | 18.44.2.46.25 |
| 18.44.2.47.5 | 18.44.2.47.13 | 18.44.2.47.18 | 18.44.2.47.22 | 18.44.2.47.25 |
| 18.44.6.1.5 | 18.44.6.1.13 | 18.44.6.1.18 | 18.44.6.1.22 | 18.44.6.1.25 |
| 18.44.6.2.5 | 18.44.6.2.13 | 18.44.6.2.18 | 18.44.6.2.22 | 18.44.6.2.25 |
| 18.44.6.5.5 | 18.44.6.5.13 | 18.44.6.5.18 | 18.44.6.5.22 | 18.44.6.5.25 |
| 18.44.6.7.5 | 18.44.6.7.13 | 18.44.6.7.18 | 18.44.6.7.22 | 18.44.6.7.25 |
| 18.44.6.46.5 | 18.44.6.46.13 | 18.44.6.46.18 | 18.44.6.46.22 | 18.44.6.46.25 |
| 18.44.6.47.5 | 18.44.6.47.13 | 18.44.6.47.18 | 18.44.6.47.22 | 18.44.6.47.25 |
| 18.44.7.1.5 | 18.44.7.1.13 | 18.44.7.1.18 | 18.44.7.1.22 | 18.44.7.1.25 |
| 18.44.7.2.5 | 18.44.7.2.13 | 18.44.7.2.18 | 18.44.7.2.22 | 18.44.7.2.25 |
| 18.44.7.5.5 | 18.44.7.5.13 | 18.44.7.5.18 | 18.44.7.5.22 | 18.44.7.5.25 |
| 18.44.7.7.5 | 18.44.7.7.13 | 18.44.7.7.18 | 18.44.7.7.22 | 18.44.7.7.25 |
| 18.44.7.46.5 | 18.44.7.46.13 | 18.44.7.46.18 | 18.44.7.46.22 | 18.44.7.46.25 |
| 18.44.7.47.5 | 18.44.7.47.13 | 18.44.7.47.18 | 18.44.7.47.22 | 18.44.7.47.25 |
| 18.44.8.1.5 | 18.44.8.1.13 | 18.44.8.1.18 | 18.44.8.1.22 | 18.44.8.1.25 |
| 18.44.8.2.5 | 18.44.8.2.13 | 18.44.8.2.18 | 18.44.8.2.22 | 18.44.8.2.25 |
| 18.44.8.5.5 | 18.44.8.5.13 | 18.44.8.5.18 | 18.44.8.5.22 | 18.44.8.5.25 |
| 18.44.8.7.5 | 18.44.8.7.13 | 18.44.8.7.18 | 18.44.8.7.22 | 18.44.8.7.25 |
| 18.44.8.46.5 | 18.44.8.46.13 | 18.44.8.46.18 | 18.44.8.46.22 | 18.44.8.46.25 |
| 18.44.8.47.5 | 18.44.8.47.13 | 18.44.8.47.18 | 18.44.8.47.22 | 18.44.8.47.25 |
| 18.44.9.1.5 | 18.44.9.1.13 | 18.44.9.1.18 | 18.44.9.1.22 | 18.44.9.1.25 |
| 18.44.9.2.5 | 18.44.9.2.13 | 18.44.9.2.18 | 18.44.9.2.22 | 18.44.9.2.25 |

TABLE 1-continued

Exemplary Enumerated Compounds

| | | | | |
|---|---|---|---|---|
| 18.44.9.5.5 | 18.44.9.5.13 | 18.44.9.5.18 | 18.44.9.5.22 | 18.44.9.5.25 |
| 18.44.9.7.5 | 18.44.9.7.13 | 18.44.9.7.18 | 18.44.9.7.22 | 18.44.9.7.25 |
| 18.44.9.46.5 | 18.44.9.46.13 | 18.44.9.46.18 | 18.44.9.46.22 | 18.44.9.46.25 |
| 18.44.9.47.5 | 18.44.9.47.13 | 18.44.9.47.18 | 18.44.9.47.22 | 18.44.9.47.25 |
| 18.44.10.1.5 | 18.44.10.1.13 | 18.44.10.1.18 | 18.44.10.1.22 | 18.44.10.1.25 |
| 18.44.10.2.5 | 18.44.10.2.13 | 18.44.10.2.18 | 18.44.10.2.22 | 18.44.10.2.25 |
| 18.44.10.5.5 | 18.44.10.5.13 | 18.44.10.5.18 | 18.44.10.5.22 | 18.44.10.5.25 |
| 18.44.10.7.5 | 18.44.10.7.13 | 18.44.10.7.18 | 18.44.10.7.22 | 18.44.10.7.25 |
| 18.44.10.46.5 | 18.44.10.46.13 | 18.44.10.46.18 | 18.44.10.46.22 | 18.44.10.46.25 |
| 18.44.10.47.5 | 18.44.10.47.13 | 18.44.10.47.18 | 18.44.10.47.22 | 18.44.10.47.25 |
| 19.43.1.1.5 | 19.43.1.1.13 | 19.43.1.1.18 | 19.43.1.1.22 | 19.43.1.1.25, |
| 19.43.1.2.5 | 19.43.1.2.13 | 19.43.1.2.18 | 19.43.1.2.22 | 19.43.1.2.25 |
| 19.43.1.5.5 | 19.43.1.5.13 | 19.43.1.5.18 | 19.43.1.5.22 | 19.43.1.5.25 |
| 19.43.1.7.5 | 19.43.1.7.13 | 19.43.1.7.18 | 19.43.1.7.22 | 19.43.1.7.25 |
| 19.43.1.46.5 | 19.43.1.46.13 | 19.43.1.46.18 | 19.43.1.46.22 | 19.43.1.46.25 |
| 19.43.1.47.5 | 19.43.1.47.13 | 19.43.1.47.18 | 19.43.1.47.22 | 19.43.1.47.25 |
| 19.43.2.1.5 | 19.43.2.1.13 | 19.43.2.1.18 | 19.43.2.1.22 | 19.43.2.1.25 |
| 19.43.2.2.5 | 19.43.2.2.13 | 19.43.2.2.18 | 19.43.2.2.22 | 19.43.2.2.25 |
| 19.43.2.5.5 | 19.43.2.5.13 | 19.43.2.5.18 | 19.43.2.5.22 | 19.43.2.5.25 |
| 19.43.2.7.5 | 19.43.2.7.13 | 19.43.2.7.18 | 19.43.2.7.22 | 19.43.2.7.25 |
| 19.43.2.46.5 | 19.43.2.46.13 | 19.43.2.46.18 | 19.43.2.46.22 | 19.43.2.46.25 |
| 19.43.2.47.5 | 19.43.2.47.13 | 19.43.2.47.18 | 19.43.2.47.22 | 19.43.2.47.25 |
| 19.43.6.1.5 | 19.43.6.1.13 | 19.43.6.1.18 | 19.43.6.1.22 | 19.43.6.1.25 |
| 19.43.6.2.5 | 19.43.6.2.13 | 19.43.6.2.18 | 19.43.6.2.22 | 19.43.6.2.25 |
| 19.43.6.5.5 | 19.43.6.5.13 | 19.43.6.5.18 | 19.43.6.5.22 | 19.43.6.5.25 |
| 19.43.6.7.5 | 19.43.6.7.13 | 19.43.6.7.18 | 19.43.6.7.22 | 19.43.6.7.25 |
| 19.43.6.46.5 | 19.43.6.46.13 | 19.43.6.46.18 | 19.43.6.46.22 | 19.43.6.46.25 |
| 19.43.6.47.5 | 19.43.6.47.13 | 19.43.6.47.18 | 19.43.6.47.22 | 19.43.6.47.25 |
| 19.43.7.1.5 | 19.43.7.1.13 | 19.43.7.1.18 | 19.43.7.1.22 | 19.43.7.1.25 |
| 19.43.7.2.5 | 19.43.7.2.13 | 19.43.7.2.18 | 19.43.7.2.22 | 19.43.7.2.25 |
| 19.43.7.5.5 | 19.43.7.5.13 | 19.43.7.5.18 | 19.43.7.5.22 | 19.43.7.5.25 |
| 19.43.7.7.5 | 19.43.7.7.13 | 19.43.7.7.18 | 19.43.7.7.22 | 19.43.7.7.25 |
| 19.43.7.46.5 | 19.43.7.46.13 | 19.43.7.46.18 | 19.43.7.46.22 | 19.43.7.46.25 |
| 19.43.7.47.5 | 19.43.7.47.13 | 19.43.7.47.18 | 19.43.7.47.22 | 19.43.7.47.25 |
| 19.43.8.1.5 | 19.43.8.1.13 | 19.43.8.1.18 | 19.43.8.1.22 | 19.43.8.1.25 |
| 19.43.8.2.5 | 19.43.8.2.13 | 19.43.8.2.18 | 19.43.8.2.22 | 19.43.8.2.25 |
| 19.43.8.5.5 | 19.43.8.5.13 | 19.43.8.5.18 | 19.43.8.5.22 | 19.43.8.5.25 |
| 19.43.8.7.5 | 19.43.8.7.13 | 19.43.8.7.18 | 19.43.8.7.22 | 19.43.8.7.25 |
| 19.43.8.46.5 | 19.43.8.46.13 | 19.43.8.46.18 | 19.43.8.46.22 | 19.43.8.46.25 |
| 19.43.8.47.5 | 19.43.8.47.13 | 19.43.8.47.18 | 19.43.8.47.22 | 19.43.8.47.25 |
| 19.43.9.1.5 | 19.43.9.1.13 | 19.43.9.1.18 | 19.43.9.1.22 | 19.43.9.1.25 |
| 19.43.9.2.5 | 19.43.9.2.13 | 19.43.9.2.18 | 19.43.9.2.22 | 19.43.9.2.25 |
| 19.43.9.5.5 | 19.43.9.5.13 | 19.43.9.5.18 | 19.43.9.5.22 | 19.43.9.5.25 |
| 19.43.9.7.5 | 19.43.9.7.13 | 19.43.9.7.18 | 19.43.9.7.22 | 19.43.9.7.25 |
| 19.43.9.46.5 | 19.43.9.46.13 | 19.43.9.46.18 | 19.43.9.46.22 | 19.43.9.46.25 |
| 19.43.9.47.5 | 19.43.9.47.13 | 19.43.9.47.18 | 19.43.9.47.22 | 19.43.9.47.25 |
| 19.43.10.1.5 | 19.43.10.1.13 | 19.43.10.1.18 | 19.43.10.1.22 | 19.43.10.1.25 |
| 19.43.10.2.5 | 19.43.10.2.13 | 19.43.10.2.18 | 19.43.10.2.22 | 19.43.10.2.25 |
| 19.43.10.5.5 | 19.43.10.5.13 | 19.43.10.5.18 | 19.43.10.5.22 | 19.43.10.5.25 |
| 19.43.10.7.5 | 19.43.10.7.13 | 19.43.10.7.18 | 19.43.10.7.22 | 19.43.10.7.25 |
| 19.43.10.46.5 | 19.43.10.46.13 | 19.43.10.46.18 | 19.43.10.46.22 | 19.43.10.46.25 |
| 19.43.10.47.5 | 19.43.10.47.13 | 19.43.10.47.18 | 19.43.10.47.22 | 19.43.10.47.25 |
| 19.44.1.1.5 | 19.44.1.1.13 | 19.44.1.1.18 | 19.44.1.1.22 | 19.44.1.1.25 |
| 19.44.1.2.5 | 19.44.1.2.13 | 19.44.1.2.18 | 19.44.1.2.22 | 19.44.1.2.25 |
| 19.44.1.5.5 | 19.44.1.5.13 | 19.44.1.5.18 | 19.44.1.5.22 | 19.44.1.5.25 |
| 19.44.1.7.5 | 19.44.1.7.13 | 19.44.1.7.18 | 19.44.1.7.22 | 19.44.1.7.25 |
| 19.44.1.46.5 | 19.44.1.46.13 | 19.44.1.46.18 | 19.44.1.46.22 | 19.44.1.46.25 |
| 19.44.1.47.5 | 19.44.1.47.13 | 19.44.1.47.18 | 19.44.1.47.22 | 19.44.1.47.25 |
| 19.44.2.1.5 | 19.44.2.1.13 | 19.44.2.1.18 | 19.44.2.1.22 | 19.44.2.1.25 |
| 19.44.2.2.5 | 19.44.2.2.13 | 19.44.2.2.18 | 19.44.2.2.22 | 19.44.2.2.25 |
| 19.44.2.5.5 | 19.44.2.5.13 | 19.44.2.5.18 | 19.44.2.5.22 | 19.44.2.5.25 |
| 19.44.2.7.5 | 19.44.2.7.13 | 19.44.2.7.18 | 19.44.2.7.22 | 19.44.2.7.25 |
| 19.44.2.46.5 | 19.44.2.46.13 | 19.44.2.46.18 | 19.44.2.46.22 | 19.44.2.46.25 |
| 19.44.2.47.5 | 19.44.2.47.13 | 19.44.2.47.18 | 19.44.2.47.22 | 19.44.2.47.25 |
| 19.44.6.1.5 | 19.44.6.1.13 | 19.44.6.1.18 | 19.44.6.1.22 | 19.44.6.1.25 |
| 19.44.6.2.5 | 19.44.6.2.13 | 19.44.6.2.18 | 19.44.6.2.22 | 19.44.6.2.25 |
| 19.44.6.5.5 | 19.44.6.5.13 | 19.44.6.5.18 | 19.44.6.5.22 | 19.44.6.5.25 |
| 19.44.6.7.5 | 19.44.6.7.13 | 19.44.6.7.18 | 19.44.6.7.22 | 19.44.6.7.25 |
| 19.44.6.46.5 | 19.44.6.46.13 | 19.44.6.46.18 | 19.44.6.46.22 | 19.44.6.46.25 |
| 19.44.6.47.5 | 19.44.6.47.13 | 19.44.6.47.18 | 19.44.6.47.22 | 19.44.6.47.25 |
| 19.44.7.1.5 | 19.44.7.1.13 | 19.44.7.1.18 | 19.44.7.1.22 | 19.44.7.1.25 |
| 19.44.7.2.5 | 19.44.7.2.13 | 19.44.7.2.18 | 19.44.7.2.22 | 19.44.7.2.25 |
| 19.44.7.5.5 | 19.44.7.5.13 | 19.44.7.5.18 | 19.44.7.5.22 | 19.44.7.5.25 |
| 19.44.7.7.5 | 19.44.7.7.13 | 19.44.7.7.18 | 19.44.7.7.22 | 19.44.7.7.25 |
| 19.44.7.46.5 | 19.44.7.46.13 | 19.44.7.46.18 | 19.44.7.46.22 | 19.44.7.46.25 |
| 19.44.7.47.5 | 19.44.7.47.13 | 19.44.7.47.18 | 19.44.7.47.22 | 19.44.7.47.25 |
| 19.44.8.1.5 | 19.44.8.1.13 | 19.44.8.1.18 | 19.44.8.1.22 | 19.44.8.1.25 |

TABLE 1-continued

Exemplary Enumerated Compounds

| | | | | |
|---|---|---|---|---|
| 19.44.8.2.5 | 19.44.8.2.13 | 19.44.8.2.18 | 19.44.8.2.22 | 19.44.8.2.25 |
| 19.44.8.5.5 | 19.44.8.5.13 | 19.44.8.5.18 | 19.44.8.5.22 | 19.44.8.5.25 |
| 19.44.8.7.5 | 19.44.8.7.13 | 19.44.8.7.18 | 19.44.8.7.22 | 19.44.8.7.25 |
| 19.44.8.46.5 | 19.44.8.46.13 | 19.44.8.46.18 | 19.44.8.46.22 | 19.44.8.46.25 |
| 19.44.8.47.5 | 19.44.8.47.13 | 19.44.8.47.18 | 19.44.8.47.22 | 19.44.8.47.25 |
| 19.44.9.1.5 | 19.44.9.1.13 | 19.44.9.1.18 | 19.44.9.1.22 | 19.44.9.1.25 |
| 19.44.9.2.5 | 19.44.9.2.13 | 19.44.9.2.18 | 19.44.9.2.22 | 19.44.9.2.25 |
| 19.44.9.5.5 | 19.44.9.5.13 | 19.44.9.5.18 | 19.44.9.5.22 | 19.44.9.5.25 |
| 19.44.9.7.5 | 19.44.9.7.13 | 19.44.9.7.18 | 19.44.9.7.22 | 19.44.9.7.25 |
| 19.44.9.46.5 | 19.44.9.46.13 | 19.44.9.46.18 | 19.44.9.46.22 | 19.44.9.46.25 |
| 19.44.9.47.5 | 19.44.9.47.13 | 19.44.9.47.18 | 19.44.9.47.22 | 19.44.9.47.25 |
| 19.44.10.1.5 | 19.44.10.1.13 | 19.44.10.1.18 | 19.44.10.1.22 | 19.44.10.1.25 |
| 19.44.10.2.5 | 19.44.10.2.13 | 19.44.10.2.18 | 19.44.10.2.22 | 19.44.10.2.25 |
| 19.44.10.5.5 | 19.44.10.5.13 | 19.44.10.5.18 | 19.44.10.5.22 | 19.44.10.5.25 |
| 19.44.10.7.5 | 19.44.10.7.13 | 19.44.10.7.18 | 19.44.10.7.22 | 19.44.10.7.25 |
| 19.44.10.46.5 | 19.44.10.46.13 | 19.44.10.46.18 | 19.44.10.46.22 | 19.44.10.46.25 |
| 19.44.10.47.5 | 19.44.10.47.13 | 19.44.10.47.18 | 19.44.10.47.22 | 19.44.10.47.25 |

Wherein $R_4$, $R_6$, and m are defined above.

Another embodiment of the invention is a compound of the formula:

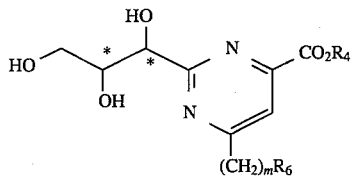

(10)

Wherein $R_4$, $R_6$, and m are defined above.

Another embodiment of the invention is a compound of the formula:

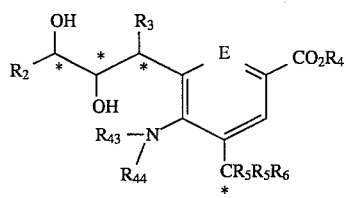

(17)

Wherein E, $R_2$, $R_3$, $R_4$, $R_5$, $R_6$, $R_{43}$, and $R_{44}$ are defined above.

Another embodiment of the invention is a compound of the formula:

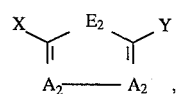

(3)

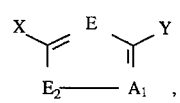

(15)

and

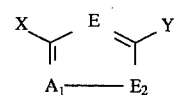

(16)

Wherein X, Y, $A_1$, $A_2$, E, and $E_2$ are defined above. In this embodiment X is not H or OH.

Another embodiment of the invention is a compound of the formula:

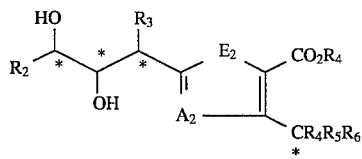

(4)

Wherein $E_2$, $R_2$, $R_3$, $R_4$, $R_5$, $R_6$, and $A_2$ are defined above.

Another embodiment of the invention is a compound of the formula:

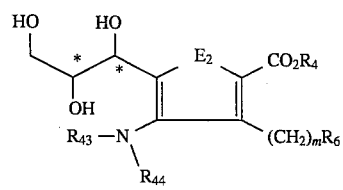

(20)

Wherein $E_2$, $R_4$, $R_6$, $R_{43}$, $R_{44}$, and m are defined above.

Another embodiment of the invention is a compound of the formula:

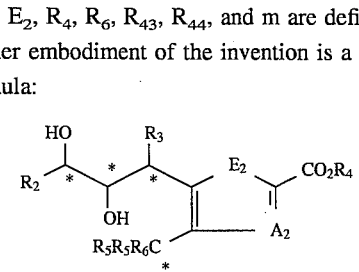

(5)

Wherein $E_2$, $R_2$, $R_3$, $R_4$, $R_5$, $R_6$, and $A_2$ are defined above.

Another embodiment of the invention is a compound of the formula:

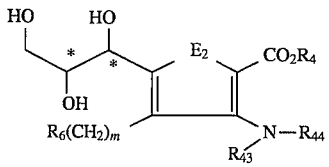

(21)

Wherein $E_2$, $R_4$, $R_6$, $R_{43}$, $R_{44}$ and m are defined above.

Another aspect of the invention is directed toward a composition comprising a compound of the formula:

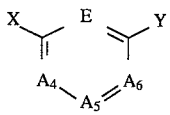

(18)

Wherein X is H or OH; and E, and Y are defined above.

$A_4$, $A_5$, and $A_6$ are each independently N, CH, $CR_{40}$ or CZ wherein $R_{40}$ is $R_{43}$, $OR_{43}$, $SR_{43}$, $S(O)R_{43}$, $S(O)_2R_{43}$, or $NR_{43}R_{44}$ wherein $R_{43}$ comprises an alkyl of 1 to 3 carbon atoms, an acyl of 2 to 3 carbon atoms, or an alkyl of 1 to 3 carbon atoms substituted with an acyl of 2 to 3 carbon atoms, and $R_{44}$ is H or an alkyl of 1 to 2 carbon atoms, and Z is a group capable of hydrogen bonding to carboxyl, or a group comprising a basic heteroatom, a protected basic heteroatom, or a cation, with the proviso that one of $A_4$, $A_5$, and $A_6$ is CZ and the others are N, CH, or $CR_{40}$; or one of $A_4$, $A_5$, and $A_6$ is N, CH, or $CR_{40}$ and the remaining two are adjacent and one is CH or $CR_{40}$ and the other is CZ, and CH or $CR_{40}$ is taken together with CZ to form a 5 to 7 membered heterocyclic ring comprising Z; with the further proviso that when X is OH, then E is not $CR_1$ wherein $R_1$ is OH; with the further proviso that when E is CH, X is H, Y is $CO_2H$, $A_4$ is $N(H)C(O)CH_3$, and $A_6$ is CH, then $A_5$ is not $CNH_2$ or $CNO_2$; and with the further proviso that when E is CH, X is OH, Y is $CO_2H$, $A_4$ is $N(H)C(O)CH_3$, and $A_6$ is CH, then $A_5$ is not $CNH_2$.

Another aspect of the invention is directed toward a composition comprising a compound is of the formula:

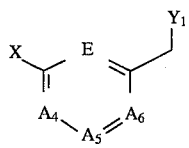

(22)

Wherein $Y_1$ is $CO_2R_4$, $C(O)N(R_4)_2$, $SO_3R_4$ or $P(O)(OR_4)_2$. E, X, $A_4$, $A_5$, $A_6$, and $R_4$ are defined above.

Another aspect of the invention is directed toward a composition comprising a compound is of the formula:

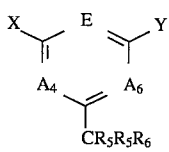

(23)

Wherein E, X, Y, $A_4$, $A_6$, $R_5$ and $R_6$ are defined above.

Another aspect of the invention is directed toward a composition comprising a compound is of the formula:

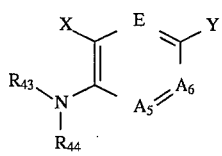

(24)

Wherein E, X, Y, $A_5$, $A_6$, $R_{43}$ and $R_{44}$ are defined above.

Another aspect of the invention is directed toward a composition comprising a compound is of the formula:

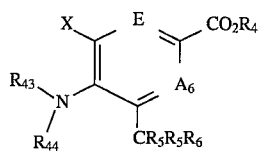

(19)

Wherein E, X, $A_6$, $R_4$, $R_5$, $R_6$, $R_{43}$, and $R_{44}$ are defined above.

The compounds of the invention are enriched or resolved optical isomers at any or all asymmetric atom. For example, the chiral centers designated by "*" in the depictions are provided as the chiral isomers or racemic mixtures. Both racemic and diastereomeric mixtures of these isomers which may exist for certain compounds, as well as the individual optical isomers isolated or synthesized, being substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. For example, ene-amine tautomers can exist for imidazole, guanine, amidine, and tetrazole systems and all the possible tautomeric forms of either are within the scope of the invention.

The compositions of this invention optionally comprise pharmaceutically acceptable non-toxic salts of the compounds herein, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety, typically the Y group carboxylic acid.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$ or organic sulfonic acids, with basic centers, typically group Z amines. Finally, it is to be understood that the compositions herein comprise compounds of the invention in their un-ionized, as well as zwitterionic form.

The compounds of the invention may be optimized to exhibit desired pharmaco-properties (as used herein pharmaco-dynamic, pharmaco-kinetic, bioavailability, or the like). One method of optimization is the modification of functional groups in particular amino and carboxyl groups to form materials having improve pharmaco-properties. Such modifications generally lead to compounds having hydrolyzable bonds at former acidic or basic sites.

Exemplary Enumerated Compounds.

By way of example and not limitation, a number of exemplary enumerated compounds of the invention are listed below. Generally, the compositions of the invention are depicted by the structures of formulas (1), (3), (15) or (16).

The compounds of the invention included in these exemplary compounds are designated by numerical format in which the first digit is the structure (1), (3), (15) or (16) carbocycle or heterocycle as numbered in FIGS. 1a–1b, the second digit represents X of FIGS. 2a–c, the third digit represents Y of FIG. 3, the fourth digit represents Z of FIGS. 4a–c, and the fifth digit when present represents $R_{40}$ of FIG. 5a–b.

The carbocyclic or heterocyclic fragments from FIGS. 1a or 1b have groups $Q_1$, $Q_2$, $Q_3$, and optionally, $Q_4$ as shown. These are the attachment points for the groups X, Y, Z, and, optionally, $R_{40}$ respectively. Each of the group fragments from FIGS. 2–4 have groups $Q_1$, $Q_2$, $Q_3$, and, optionally, $Q_4$ shown, respectively. These are the points of attachment to the corresponding $Q_1$, $Q_2$, $Q_3$, or $Q_4$ groups shown on the carbocyclic or heterocyclic fragment. By attachment it is intended that the two groups $Q_1$, the two groups $Q_2$, the two groups $Q_3$ and, when present, the two groups $Q_4$ are combined to form a chemical bond. In this manner the groups (one each from FIGS. 1–4, and when present, one from FIGS. 5) are combined to produce a single chemical formula (or structure) representing the compound named according to the above description.

By way of example, three compounds having the designation 2.19.1.1, 7.5.5.36, 12.5.5.36 and 17.34.10.1.22 are shown below. Note in particular that 7.5.5.36 and 12.5.5.36 have the same X, Y, and Z groups and differ only in the aromatic core. The stereochemistry of the methyl substituent is preserved in the two compounds.

Table 1 is a list of exemplary enumerated compounds of the invention.

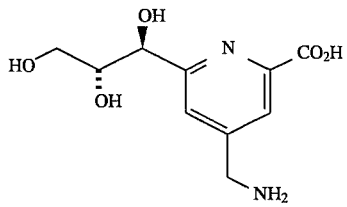
2.19.1.1

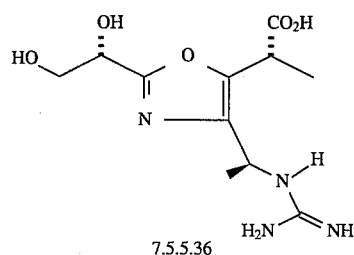
7.5.5.36

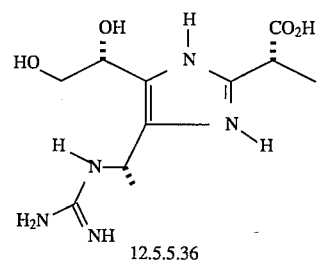
12.5.5.36

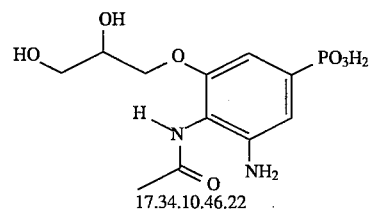
17.34.10.46.22

TABLE 1

Exemplary Enumerated Compounds

| | | | | |
|---|---|---|---|---|
| 17.43.1.1.5 | 17.43.1.1.13 | 17.43.1.1.18 | 17.43.1.1.22 | 17.43.1.1.25 |
| 17.43.1.2.5 | 17.43.1.2.13 | 17.43.1.2.18 | 17.43.1.2.22 | 17.43.1.2.25 |
| 17.43.1.5.5 | 17.43.1.5.13 | 17.43.1.5.18 | 17.43.1.5.22 | 17.43.1.5.25 |
| 17.43.1.7.5 | 17.43.1.7.13 | 17.43.1.7.18 | 17.43.1.7.22 | 17.43.1.7.25 |
| 17.43.1.46.5 | 17.43.1.46.13 | 17.43.1.46.18 | 17.43.1.46.22 | 17.43.1.46.25 |
| 17.43.1.47.5 | 17.43.1.47.13 | 17.43.1.47.18 | 17.43.1.47.22 | 17.43.1.47.25 |
| 17.43.2.1.5 | 17.43.2.1.13 | 17.43.2.1.18 | 17.43.2.1.22 | 17.43.2.1.25 |
| 17.43.2.2.5 | 17.43.2.2.13 | 17.43.2.2.18 | 17.43.2.2.22 | 17.43.2.2.25 |
| 17.43.2.5.5 | 17.43.2.5.13 | 17.43.2.5.18 | 17.43.2.5.22 | 17.43.2.5.25 |
| 17.43.2.7.5 | 17.43.2.7.13 | 17.43.2.7.18 | 17.43.2.7.22 | 17.43.2.7.25 |
| 17.43.2.46.5 | 17.43.2.46.13 | 17.43.2.46.18 | 17.43.2.46.22 | 17.43.2.46.25 |
| 17.43.2.47.5 | 17.43.2.47.13 | 17.43.2.47.18 | 17.43.2.47.22 | 17.43.2.47.25 |
| 17.43.6.1.5 | 17.43.6.1.13 | 17.43.6.1.18 | 17.43.6.1.22 | 17.43.6.1.25 |
| 17.43.6.2.5 | 17.43.6.2.13 | 17.43.6.2.18 | 17.43.6.2.22 | 17.43.6.2.25 |
| 17.43.6.5.5 | 17.43.6.5.13 | 17.43.6.5.18 | 17.43.6.5.22 | 17.43.6.5.25 |
| 17.43.6.7.5 | 17.43.6.7.13 | 17.43.6.7.18 | 17.43.6.7.22 | 17.43.6.7.25 |
| 17.43.6.46.5 | 17.43.6.46.13 | 17.43.6.46.18 | 17.43.6.46.22 | 17.43.6.46.25 |
| 17.43.6.47.5 | 17.43.6.47.13 | 17.43.6.47.18 | 17.43.6.47.22 | 17.43.6.47.25 |
| 17.43.7.1.5 | 17.43.7.1.13 | 17.43.7.1.18 | 17.43.7.1.22 | 17.43.7.1.25 |
| 17.43.7.2.5 | 17.43.7.2.13 | 17.43.7.2.18 | 17.43.7.2.22 | 17.43.7.2.25 |
| 17.43.7.5.5 | 17.43.7.5.13 | 17.43.7.5.18 | 17.43.7.5.22 | 17.43.7.5.25 |
| 17.43.7.7.5 | 17.43.7.7.13 | 17.43.7.7.18 | 17.43.7.7.22 | 17.43.7.7.25 |
| 17.43.7.46.5 | 17.43.7.46.13 | 17.43.7.46.18 | 17.43.7.46.22 | 17.43.7.46.25 |
| 17.43.7.47.5 | 17.43.7.47.13 | 17.43.7.47.18 | 17.43.7.47.22 | 17.43.7.47.25 |
| 17.43.8.1.5 | 17.43.8.1.13 | 17.43.8.1.18 | 17.43.8.1.22 | 17.43.8.1.25 |
| 17.43.8.2.5 | 17.43.8.2.13 | 17.43.8.2.18 | 17.43.8.2.22 | 17.43.8.2.25 |
| 17.43.8.5.5 | 17.43.8.5.13 | 17.43.8.5.18 | 17.43.8.5.22 | 17.43.8.5.25 |
| 17.43.8.7.5 | 17.43.8.7.13 | 17.43.8.7.18 | 17.43.8.7.22 | 17.43.8.7.25 |
| 17.43.8.46.5 | 17.43.8.46.13 | 17.43.8.46.18 | 17.43.8.46.22 | 17.43.8.46.25 |

TABLE 1-continued

Exemplary Enumerated Compounds

| | | | | |
|---|---|---|---|---|
| 17.43.8.47.5 | 17.43.8.47.13 | 17.43.8.47.18 | 17.43.8.47.22 | 17.43.8.47.25 |
| 17.43.9.1.5 | 17.43.9.1.13 | 17.43.9.1.18 | 17.43.9.1.22 | 17.43.9.1.25 |
| 17.43.9.2.5 | 17.43.9.2.13 | 17.43.9.2.18 | 17.43.9.2.22 | 17.43.9.2.25 |
| 17.43.9.5.5 | 17.43.9.5.13 | 17.43.9.5.18 | 17.43.9.5.22 | 17.43.9.5.25 |
| 17.43.9.7.5 | 17.43.9.7.13 | 17.43.9.7.18 | 17.43.9.7.22 | 17.43.9.7.25 |
| 17.43.9.46.5 | 17.43.9.46.13 | 17.43.9.46.18 | 17.43.9.46.22 | 17.43.9.46.25 |
| 17.43.9.47.5 | 17.43.9.47.13 | 17.43.9.47.18 | 17.43.9.47.22 | 17.43.9.47.25 |
| 17.43.10.1.5 | 17.43.10.1.13 | 17.43.10.1.18 | 17.43.10.1.22 | 17.43.10.1.25 |
| 17.43.10.2.5 | 17.43.10.2.13 | 17.43.10.2.18 | 17.43.10.2.22 | 17.43.10.2.25 |
| 17.43.10.5.5 | 17.43.10.5.13 | 17.43.10.5.18 | 17.43.10.5.22 | 17.43.10.5.25 |
| 17.43.10.7.5 | 17.43.10.7.13 | 17.43.10.7.18 | 17.43.10.7.22 | 17.43.10.7.25 |
| 17.43.10.46.5 | 17.43.10.46.13 | 17.43.10.46.18 | 17.43.10.46.22 | 17.43.10.46.25 |
| 17.43.10.47.5 | 17.43.10.47.13 | 17.43.10.47.18 | 17.43.10.47.22 | 17.43.10.47.25 |
| 17.44.1.1.5 | 17.44.1.1.13 | 17.44.1.1.18 | 17.44.1.1.22 | 17.44.1.1.25 |
| 17.44.1.2.5 | 17.44.1.2.13 | 17.44.1.2.18 | 17.44.1.2.22 | 17.44.1.2.25 |
| 17.44.1.5.5 | 17.44.1.5.13 | 17.44.1.5.18 | 17.44.1.5.22 | 17.44.1.5.25 |
| 17.44.1.7.5 | 17.44.1.7.13 | 17.44.1.7.18 | 17.44.1.7.22 | 17.44.1.7.25 |
| 17.44.1.46.5 | 17.44.1.46.13 | 17.44.1.46.18 | 17.44.1.46.22 | 17.44.1.46.25 |
| 17.44.1.47.5 | 17.44.1.47.13 | 17.44.1.47.18 | 17.44.1.47.22 | 17.44.1.47.25 |
| 17.44.2.1.5 | 17.44.2.1.13 | 17.44.2.1.18 | 17.44.2.1.22 | 17.44.2.1.25 |
| 17.44.2.2.5 | 17.44.2.2.13 | 17.44.2.2.18 | 17.44.2.2.22 | 17.44.2.2.25 |
| 17.44.2.5.5 | 17.44.2.5.13 | 17.44.2.5.18 | 17.44.2.5.22 | 17.44.2.5.25 |
| 17.44.2.7.5 | 17.44.2.7.13 | 17.44.2.7.18 | 17.44.2.7.22 | 17.44.2.7.25 |
| 17.44.2.46.5 | 17.44.2.46.13 | 17.44.2.46.18 | 17.44.2.46.22 | 17.44.2.46.25 |
| 17.44.2.47.5 | 17.44.2.47.13 | 17.44.2.47.18 | 17.44.2.47.22 | 17.44.2.47.25 |
| 17.44.6.1.5 | 17.44.6.1.13 | 17.44.6.1.18 | 17.44.6.1.22 | 17.44.6.1.25 |
| 17.44.6.2.5 | 17.44.6.2.13 | 17.44.6.2.18 | 17.44.6.2.22 | 17.44.6.2.25 |
| 17.44.6.5.5 | 17.44.6.5.13 | 17.44.6.5.18 | 17.44.6.5.22 | 17.44.6.5.25 |
| 17.44.6.7.5 | 17.44.6.7.13 | 17.44.6.7.18 | 17.44.6.7.22 | 17.44.6.7.25 |
| 17.44.6.46.5 | 17.44.6.46.13 | 17.44.6.46.18 | 17.44.6.46.22 | 17.44.6.46.25 |
| 17.44.6.47.5 | 17.44.6.47.13 | 17.44.6.47.18 | 17.44.6.47.22 | 17.44.6.47.25 |
| 17.44.7.1.5 | 17.44.7.1.13 | 17.44.7.1.18 | 17.44.7.1.22 | 17.44.7.1.25 |
| 17.44.7.2.5 | 17.44.7.2.13 | 17.44.7.2.18 | 17.44.7.2.22 | 17.44.7.2.25 |
| 17.44.7.5.5 | 17.44.7.5.13 | 17.44.7.5.18 | 17.44.7.5.22 | 17.44.7.5.25 |
| 17.44.7.7.5 | 17.44.7.7.13 | 17.44.7.7.18 | 17.44.7.7.22 | 17.44.7.7.25 |
| 17.44.7.46.5 | 17.44.7.46.13 | 17.44.7.46.18 | 17.44.7.46.22 | 17.44.7.46.25 |
| 17.44.7.47.5 | 17.44.7.47.13 | 17.44.7.47.18 | 17.44.7.47.22 | 17.44.7.47.25 |
| 17.44.8.1.5 | 17.44.8.1.13 | 17.44.8.1.18 | 17.44.8.1.22 | 17.44.8.1.25 |
| 17.44.8.2.5 | 17.44.8.2.13 | 17.44.8.2.18 | 17.44.8.2.22 | 17.44.8.2.25 |
| 17.44.8.5.5 | 17.44.8.5.13 | 17.44.8.5.18 | 17.44.8.5.22 | 17.44.8.5.25 |
| 17.44.8.7.5 | 17.44.8.7.13 | 17.44.8.7.18 | 17.44.8.7.22 | 17.44.8.7.25 |
| 17.44.8.46.5 | 17.44.8.46.13 | 17.44.8.46.18 | 17.44.8.46.22 | 17.44.8.46.25 |
| 17.44.8.47.5 | 17.44.8.47.13 | 17.44.8.47.18 | 17.44.8.47.22 | 17.44.8.47.25 |
| 17.44.9.1.5 | 17.44.9.1.13 | 17.44.9.1.18 | 17.44.9.1.22 | 17.44.9.1.25 |
| 17.44.9.2.5 | 17.44.9.2.13 | 17.44.9.2.18 | 17.44.9.2.22 | 17.44.9.2.25 |
| 17.44.9.5.5 | 17.44.9.5.13 | 17.44.9.5.18 | 17.44.9.5.22 | 17.44.9.5.25 |
| 17.44.9.7.5 | 17.44.9.7.13 | 17.44.9.7.18 | 17.44.9.7.22 | 17.44.9.7.25 |
| 17.44.9.46.5 | 17.44.9.46.13 | 17.44.9.46.18 | 17.44.9.46.22 | 17.44.9.46.25 |
| 17.44.9.47.5 | 17.44.9.47.13 | 17.44.9.47.18 | 17.44.9.47.22 | 17.44.9.47.25 |
| 17.44.10.1.5 | 17.44.10.1.13 | 17.44.10.1.18 | 17.44.10.1.22 | 17.44.10.1.25 |
| 17.44.10.2.5 | 17.44.10.2.13 | 17.44.10.2.18 | 17.44.10.2.22 | 17.44.10.2.25 |
| 17.44.10.5.5 | 17.44.10.5.13 | 17.44.10.5.18 | 17.44.10.5.22 | 17.44.10.5.25 |
| 17.44.10.7.5 | 17.44.10.7.13 | 17.44.10.7.18 | 17.44.10.7.22 | 17.44.10.7.25 |
| 17.44.10.46.5 | 17.44.10.46.13 | 17.44.10.46.18 | 17.44.10.46.22 | 17.44.10.46.25 |
| 17.44.10.47.5 | 17.44.10.47.13 | 17.44.10.47.18 | 17.44.10.47.22 | 17.44.10.47.25 |
| 18.43.1.1.5 | 18.43.1.1.13 | 18.43.1.1.18 | 18.43.1.1.22 | 18.43.1.1.25 |
| 18.43.1.2.5 | 18.43.1.2.13 | 18.43.1.2.18 | 18.43.1.2.22 | 18.43.1.2.25 |
| 18.43.1.5.5 | 18.43.1.5.13 | 18.43.1.5.18 | 18.43.1.5.22 | 18.43.1.5.25 |
| 18.43.1.7.5 | 18.43.1.7.13 | 18.43.1.7.18 | 18.43.1.7.22 | 18.43.1.7.25 |
| 18.43.1.46.5 | 18.43.1.46.13 | 18.43.1.46.18 | 18.43.1.46.22 | 18.43.1.46.25 |
| 18.43.1.47.5 | 18.43.1.47.13 | 18.43.1.47.18 | 18.43.1.47.22 | 18.43.1.47.25 |
| 18.43.2.1.5 | 18.43.2.1.13 | 18.43.2.1.18 | 18.43.2.1.22 | 18.43.2.1.25 |
| 18.43.2.2.5 | 18.43.2.2.13 | 18.43.2.2.18 | 18.43.2.2.22 | 18.43.2.2.25 |
| 18.43.2.5.5 | 18.43.2.5.13 | 18.43.2.5.18 | 18.43.2.5.22 | 18.43.2.5.25 |
| 18.43.2.7.5 | 18.43.2.7.13 | 18.43.2.7.18 | 18.43.2.7.22 | 18.43.2.7.25 |
| 18.43.2.46.5 | 18.43.2.46.13 | 18.43.2.46.18 | 18.43.2.46.22 | 18.43.2.46.25 |
| 18.43.2.47.5 | 18.43.2.47.13 | 18.43.2.47.18 | 18.43.2.47.22 | 18.43.2.47.25 |
| 18.43.6.1.5 | 18.43.6.1.13 | 18.43.6.1.18 | 18.43.6.1.22 | 18.43.6.1.25 |
| 18.43.6.2.5 | 18.43.6.2.13 | 18.43.6.2.18 | 18.43.6.2.22 | 18.43.6.2.25 |
| 18.43.6.5.5 | 18.43.6.5.13 | 18.43.6.5.18 | 18.43.6.5.22 | 18.43.6.5.25 |
| 18.43.6.7.5 | 18.43.6.7.13 | 18.43.6.7.18 | 18.43.6.7.22 | 18.43.6.7.25 |
| 18.43.6.46.5 | 18.43.6.46.13 | 18.43.6.46.18 | 18.43.6.46.22 | 18.43.6.46.25 |
| 18.43.6.47.5 | 18.43.6.47.13 | 18.43.6.47.18 | 18.43.6.47.22 | 18.43.6.47.25 |
| 18.43.7.1.5 | 18.43.7.1.13 | 18.43.7.1.18 | 18.43.7.1.22 | 18.43.7.1.25 |
| 18.43.7.2.5 | 18.43.7.2.13 | 18.43.7.2.18 | 18.43.7.2.22 | 18.43.7.2.25 |
| 18.43.7.5.5 | 18.43.7.5.13 | 18.43.7.5.18 | 18.43.7.5.22 | 18.43.7.5.25 |
| 18.43.7.7.5 | 18.43.7.7.13 | 18.43.7.7.18 | 18.43.7.7.22 | 18.43.7.7.25 |

TABLE 1-continued

Exemplary Enumerated Compounds

| | | | | |
|---|---|---|---|---|
| 18.43.7.46.5 | 18.43.7.46.13 | 18.43.7.46.18 | 18.43.7.46.22 | 18.43.7.46.25 |
| 18.43.7.47.5 | 18.43.7.47.13 | 18.43.7.47.18 | 18.43.7.47.22 | 18.43.7.47.25 |
| 18.43.8.1.5 | 18.43.8.1.13 | 18.43.8.1.18 | 18.43.8.1.22 | 18.43.8.1.25 |
| 18.43.8.2.5 | 18.43.8.2.13 | 18.43.8.2.18 | 18.43.8.2.22 | 18.43.8.2.25 |
| 18.43.8.5.5 | 18.43.8.5.13 | 18.43.8.5.18 | 18.43.8.5.22 | 18.43.8.5.25 |
| 18.43.8.7.5 | 18.43.8.7.13 | 18.43.8.7.18 | 18.43.8.7.22 | 18.43.8.7.25 |
| 18.43.8.46.5 | 18.43.8.46.13 | 18.43.8.46.18 | 18.43.8.46.22 | 18.43.8.46.25 |
| 18.43.8.47.5 | 18.43.8.47.13 | 18.43.8.47.18 | 18.43.8.47.22 | 18.43.8.47.25 |
| 18.43.9.1.5 | 18.43.9.1.13 | 18.43.9.1.18 | 18.43.9.1.22 | 18.43.9.1.25 |
| 18.43.9.2.5 | 18.43.9.2.13 | 18.43.9.2.18 | 18.43.9.2.22 | 18.43.9.2.25 |
| 18.43.9.5.5 | 18.43.9.5.13 | 18.43.9.5.18 | 18.43.9.5.22 | 18.43.9.5.25 |
| 18.43.9.7.5 | 18.43.9.7.13 | 18.43.9.7.18 | 18.43.9.7.22 | 18.43.9.7.25 |
| 18.43.9.46.5 | 18.43.9.46.13 | 18.43.9.46.18 | 18.43.9.46.22 | 18.43.9.46.25 |
| 18.43.9.47.5 | 18.43.9.47.13 | 18.43.9.47.18 | 18.43.9.47.22 | 18.43.9.47.25 |
| 18.43.10.1.5 | 18.43.10.1.13 | 18.43.10.1.18 | 18.43.10.1.22 | 18.43.10.1.25 |
| 18.43.10.2.5 | 18.43.10.2.13 | 18.43.10.2.18 | 18.43.10.2.22 | 18.43.10.2.25 |
| 18.43.10.5.5 | 18.43.10.5.13 | 18.43.10.5.18 | 18.43.10.5.22 | 18.43.10.5.25 |
| 18.43.10.7.5 | 18.43.10.7.13 | 18.43.10.7.18 | 18.43.10.7.22 | 18.43.10.7.25 |
| 18.43.10.46.5 | 18.43.10.46.13 | 18.43.10.46.18 | 18.43.10.46.22 | 18.43.10.46.25 |
| 18.43.10.47.5 | 18.43.10.47.13 | 18.43.10.47.18 | 18.43.10.47.22 | 18.43.10.47.25 |
| 18.44.1.1.5 | 18.44.1.1.13 | 18.44.1.1.18 | 18.44.1.1.22 | 18.44.1.1.25 |
| 18.44.1.2.5 | 18.44.1.2.13 | 18.44.1.2.18 | 18.44.1.2.22 | 18.44.1.2.25 |
| 18.44.1.5.5 | 18.44.1.5.13 | 18.44.1.5.18 | 18.44.1.5.22 | 18.44.1.5.25 |
| 18.44.1.7.5 | 18.44.1.7.13 | 18.44.1.7.18 | 18.44.1.7.22 | 18.44.1.7.25 |
| 18.44.1.46.5 | 18.44.1.46.13 | 18.44.1.46.18 | 18.44.1.46.22 | 18.44.1.46.25 |
| 18.44.1.47.5 | 18.44.1.47.13 | 18.44.1.47.18 | 18.44.1.47.22 | 18.44.1.47.25 |
| 18.44.2.1.5 | 18.44.2.1.13 | 18.44.2.1.18 | 18.44.2.1.22 | 18.44.2.1.25 |
| 18.44.2.2.5 | 18.44.2.2.13 | 18.44.2.2.18 | 18.44.2.2.22 | 18.44.2.2.25 |
| 18.44.2.5.5 | 18.44.2.5.13 | 18.44.2.5.18 | 18.44.2.5.22 | 18.44.2.5.25 |
| 18.44.2.7.5 | 18.44.2.7.13 | 18.44.2.7.18 | 18.44.2.7.22 | 18.44.2.7.25 |
| 18.44.2.46.5 | 18.44.2.46.13 | 18.44.2.46.18 | 18.44.2.46.22 | 18.44.2.46.25 |
| 18.44.2.47.5 | 18.44.2.47.13 | 18.44.2.47.18 | 18.44.2.47.22 | 18.44.2.47.25 |
| 18.44.6.1.5 | 18.44.6.1.13 | 18.44.6.1.18 | 18.44.6.1.22 | 18.44.6.1.25 |
| 18.44.6.2.5 | 18.44.6.2.13 | 18.44.6.2.18 | 18.44.6.2.22 | 18.44.6.2.25 |
| 18.44.6.5.5 | 18.44.6.5.13 | 18.44.6.5.18 | 18.44.6.5.22 | 18.44.6.5.25 |
| 18.44.6.7.5 | 18.44.6.7.13 | 18.44.6.7.18 | 18.44.6.7.22 | 18.44.6.7.25 |
| 18.44.6.46.5 | 18.44.6.46.13 | 18.44.6.46.18 | 18.44.6.46.22 | 18.44.6.46.25 |
| 18.44.6.47.5 | 18.44.6.47.13 | 18.44.6.47.18 | 18.44.6.47.22 | 18.44.6.47.25 |
| 18.44.7.1.5 | 18.44.7.1.13 | 18.44.7.1.18 | 18.44.7.1.22 | 18.44.7.1.25 |
| 18.44.7.2.5 | 18.44.7.2.13 | 18.44.7.2.18 | 18.44.7.2.22 | 18.44.7.2.25 |
| 18.44.7.5.5 | 18.44.7.5.13 | 18.44.7.5.18 | 18.44.7.5.22 | 18.44.7.5.25 |
| 18.44.7.7.5 | 18.44.7.7.13 | 18.44.7.7.18 | 18.44.7.7.22 | 18.44.7.7.25 |
| 18.44.7.46.5 | 18.44.7.46.13 | 18.44.7.46.18 | 18.44.7.46.22 | 18.44.7.46.25 |
| 18.44.7.47.5 | 18.44.7.47.13 | 18.44.7.47.18 | 18.44.7.47.22 | 18.44.7.47.25 |
| 18.44.8.1.5 | 18.44.8.1.13 | 18.44.8.1.18 | 18.44.8.1.22 | 18.44.8.1.25 |
| 18.44.8.2.5 | 18.44.8.2.13 | 18.44.8.2.18 | 18.44.8.2.22 | 18.44.8.2.25 |
| 18.44.8.5.5 | 18.44.8.5.13 | 18.44.8.5.18 | 18.44.8.5.22 | 18.44.8.5.25 |
| 18.44.8.7.5 | 18.44.8.7.13 | 18.44.8.7.18 | 18.44.8.7.22 | 18.44.8.7.25 |
| 18.44.8.46.5 | 18.44.8.46.13 | 18.44.8.46.18 | 18.44.8.46.22 | 18.44.8.46.25 |
| 18.44.8.47.5 | 18.44.8.47.13 | 18.44.8.47.18 | 18.44.8.47.22 | 18.44.8.47.25 |
| 18.44.9.1.5 | 18.44.9.1.13 | 18.44.9.1.18 | 18.44.9.1.22 | 18.44.9.1.25 |
| 18.44.9.2.5 | 18.44.9.2.13 | 18.44.9.2.18 | 18.44.9.2.22 | 18.44.9.2.25 |
| 18.44.9.5.5 | 18.44.9.5.13 | 18.44.9.5.18 | 18.44.9.5.22 | 18.44.9.5.25 |
| 18.44.9.7.5 | 18.44.9.7.13 | 18.44.9.7.18 | 18.44.9.7.22 | 18.44.9.7.25 |
| 18.44.9.46.5 | 18.44.9.46.13 | 18.44.9.46.18 | 18.44.9.46.22 | 18.44.9.46.25 |
| 18.44.9.47.5 | 18.44.9.47.13 | 18.44.9.47.18 | 18.44.9.47.22 | 18.44.9.47.25 |
| 18.44.10.1.5 | 18.44.10.1.13 | 18.44.10.1.18 | 18.44.10.1.22 | 18.44.10.1.25 |
| 18.44.10.2.5 | 18.44.10.2.13 | 18.44.10.2.18 | 18.44.10.2.22 | 18.44.10.2.25 |
| 18.44.10.5.5 | 18.44.10.5.13 | 18.44.10.5.18 | 18.44.10.5.22 | 18.44.10.5.25 |
| 18.44.10.7.5 | 18.44.10.7.13 | 18.44.10.7.18 | 18.44.10.7.22 | 18.44.10.7.25 |
| 18.44.10.46.5 | 18.44.10.46.13 | 18.44.10.46.18 | 18.44.10.46.22 | 18.44.10.46.25 |
| 18.44.10.47.5 | 18.44.10.47.13 | 18.44.10.47.18 | 18.44.10.47.22 | 18.44.10.47.25 |
| 19.43.1.1.5 | 19.43.1.1.13 | 19.43.1.1.18 | 19.43.1.1.22 | 19.43.1.1.25, |
| 19.43.1.2.5 | 19.43.1.2.13 | 19.43.1.2.18 | 19.43.1.2.22 | 19.43.1.2.25 |
| 19.43.1.5.5 | 19.43.1.5.13 | 19.43.1.5.18 | 19.43.1.5.22 | 19.43.1.5.25 |
| 19.43.1.7.5 | 19.43.1.7.13 | 19.43.1.7.18 | 19.43.1.7.22 | 19.43.1.7.25 |
| 19.43.1.46.5 | 19.43.1.46.13 | 19.43.1.46.18 | 19.43.1.46.22 | 19.43.1.46.25 |
| 19.43.1.47.5 | 19.43.1.47.13 | 19.43.1.47.18 | 19.43.1.47.22 | 19.43.1.47.25 |
| 19.43.2.1.5 | 19.43.2.1.13 | 19.43.2.1.18 | 19.43.2.1.22 | 19.43.2.1.25 |
| 19.43.2.2.5 | 19.43.2.2.13 | 19.43.2.2.18 | 19.43.2.2.22 | 19.43.2.2.25 |
| 19.43.2.5.5 | 19.43.2.5.13 | 19.43.2.5.18 | 19.43.2.5.22 | 19.43.2.5.25 |
| 19.43.2.7.5 | 19.43.2.7.13 | 19.43.2.7.18 | 19.43.2.7.22 | 19.43.2.7.25 |
| 19.43.2.46.5 | 19.43.2.46.13 | 19.43.2.46.18 | 19.43.2.46.22 | 19.43.2.46.25 |
| 19.43.2.47.5 | 19.43.2.47.13 | 19.43.2.47.18 | 19.43.2.47.22 | 19.43.2.47.25 |
| 19.43.6.1.5 | 19.43.6.1.13 | 19.43.6.1.18 | 19.43.6.1.22 | 19.43.6.1.25 |
| 19.43.6.2.5 | 19.43.6.2.13 | 19.43.6.2.18 | 19.43.6.2.22 | 19.43.6.2.25 |
| 19.43.6.5.5 | 19.43.6.5.13 | 19.43.6.5.18 | 19.43.6.5.22 | 19.43.6.5.25 |

TABLE 1-continued

Exemplary Enumerated Compounds

| | | | | |
|---|---|---|---|---|
| 19.43.6.7.5 | 19.43.6.7.13 | 19.43.6.7.18 | 19.43.6.7.22 | 19.43.6.7.25 |
| 19.43.6.46.5 | 19.43.6.46.13 | 19.43.6.46.18 | 19.43.6.46.22 | 19.43.6.46.25 |
| 19.43.6.47.5 | 19.43.6.47.13 | 19.43.6.47.18 | 19.43.6.47.22 | 19.43.6.47.25 |
| 19.43.7.1.5 | 19.43.7.1.13 | 19.43.7.1.18 | 19.43.7.1.22 | 19.43.7.1.25 |
| 19.43.7.2.5 | 19.43.7.2.13 | 19.43.7.2.18 | 19.43.7.2.22 | 19.43.7.2.25 |
| 19.43.7.5.5 | 19.43.7.5.13 | 19.43.7.5.18 | 19.43.7.5.22 | 19.43.7.5.25 |
| 19.43.7.7.5 | 19.43.7.7.13 | 19.43.7.7.18 | 19.43.7.7.22 | 19.43.7.7.25 |
| 19.43.7.46.5 | 19.43.7.46.13 | 19.43.7.46.18 | 19.43.7.46.22 | 19.43.7.46.25 |
| 19.43.7.47.5 | 19.43.7.47.13 | 19.43.7.47.18 | 19.43.7.47.22 | 19.43.7.47.25 |
| 19.43.8.1.5 | 19.43.8.1.13 | 19.43.8.1.18 | 19.43.8.1.22 | 19.43.8.1.25 |
| 19.43.8.2.5 | 19.43.8.2.13 | 19.43.8.2.18 | 19.43.8.2.22 | 19.43.8.2.25 |
| 19.43.8.5.5 | 19.43.8.5.13 | 19.43.8.5.18 | 19.43.8.5.22 | 19.43.8.5.25 |
| 19.43.8.7.5 | 19.43.8.7.13 | 19.43.8.7.18 | 19.43.8.7.22 | 19.43.8.7.25 |
| 19.43.8.46.5 | 19.43.8.46.13 | 19.43.8.46.18 | 19.43.8.46.22 | 19.43.8.46.25 |
| 19.43.8.47.5 | 19.43.8.47.13 | 19.43.8.47.18 | 19.43.8.47.22 | 19.43.8.47.25 |
| 19.43.9.1.5 | 19.43.9.1.13 | 19.43.9.1.18 | 19.43.9.1.22 | 19.43.9.1.25 |
| 19.43.9.2.5 | 19.43.9.2.13 | 19.43.9.2.18 | 19.43.9.2.22 | 19.43.9.2.25 |
| 19.43.9.5.5 | 19.43.9.5.13 | 19.43.9.5.18 | 19.43.9.5.22 | 19.43.9.5.25 |
| 19.43.9.7.5 | 19.43.9.7.13 | 19.43.9.7.18 | 19.43.9.7.22 | 19.43.9.7.25 |
| 19.43.9.46.5 | 19.43.9.46.13 | 19.43.9.46.18 | 19.43.9.46.22 | 19.43.9.46.25 |
| 19.43.9.47.5 | 19.43.9.47.13 | 19.43.9.47.18 | 19.43.9.47.22 | 19.43.9.47.25 |
| 19.43.10.1.5 | 19.43.10.1.13 | 19.43.10.1.18 | 19.43.10.1.22 | 19.43.10.1.25 |
| 19.43.10.2.5 | 19.43.10.2.13 | 19.43.10.2.18 | 19.43.10.2.22 | 19.43.10.2.25 |
| 19.43.10.5.5 | 19.43.10.5.13 | 19.43.10.5.18 | 19.43.10.5.22 | 19.43.10.5.25 |
| 19.43.10.7.5 | 19.43.10.7.13 | 19.43.10.7.18 | 19.43.10.7.22 | 19.43.10.7.25 |
| 19.43.10.46.5 | 19.43.10.46.13 | 19.43.10.46.18 | 19.43.10.46.22 | 19.43.10.46.25 |
| 19.43.10.47.5 | 19.43.10.47.13 | 19.43.10.47.18 | 19.43.10.47.22 | 19.43.10.47.25 |
| 19.44.1.1.5 | 19.44.1.1.13 | 19.44.1.1.18 | 19.44.1.1.22 | 19.44.1.1.25 |
| 19.44.1.2.5 | 19.44.1.2.13 | 19.44.1.2.18 | 19.44.1.2.22 | 19.44.1.2.25 |
| 19.44.1.5.5 | 19.44.1.5.13 | 19.44.1.5.18 | 19.44.1.5.22 | 19.44.1.5.25 |
| 19.44.1.7.5 | 19.44.1.7.13 | 19.44.1.7.18 | 19.44.1.7.22 | 19.44.1.7.25 |
| 19.44.1.46.5 | 19.44.1.46.13 | 19.44.1.46.18 | 19.44.1.46.22 | 19.44.1.46.25 |
| 19.44.1.47.5 | 19.44.1.47.13 | 19.44.1.47.18 | 19.44.1.47.22 | 19.44.1.47.25 |
| 19.44.2.1.5 | 19.44.2.1.13 | 19.44.2.1.18 | 19.44.2.1.22 | 19.44.2.1.25 |
| 19.44.2.2.5 | 19.44.2.2.13 | 19.44.2.2.18 | 19.44.2.2.22 | 19.44.2.2.25 |
| 19.44.2.5.5 | 19.44.2.5.13 | 19.44.2.5.18 | 19.44.2.5.22 | 19.44.2.5.25 |
| 19.44.2.7.5 | 19.44.2.7.13 | 19.44.2.7.18 | 19.44.2.7.22 | 19.44.2.7.25 |
| 19.44.2.46.5 | 19.44.2.46.13 | 19.44.2.46.18 | 19.44.2.46.22 | 19.44.2.46.25 |
| 19.44.2.47.5 | 19.44.2.47.13 | 19.44.2.47.18 | 19.44.2.47.22 | 19.44.2.47.25 |
| 19.44.6.1.5 | 19.44.6.1.13 | 19.44.6.1.18 | 19.44.6.1.22 | 19.44.6.1.25 |
| 19.44.6.2.5 | 19.44.6.2.13 | 19.44.6.2.18 | 19.44.6.2.22 | 19.44.6.2.25 |
| 19.44.6.5.5 | 19.44.6.5.13 | 19.44.6.5.18 | 19.44.6.5.22 | 19.44.6.5.25 |
| 19.44.6.7.5 | 19.44.6.7.13 | 19.44.6.7.18 | 19.44.6.7.22 | 19.44.6.7.25 |
| 19.44.6.46.5 | 19.44.6.46.13 | 19.44.6.46.18 | 19.44.6.46.22 | 19.44.6.46.25 |
| 19.44.6.47.5 | 19.44.6.47.13 | 19.44.6.47.18 | 19.44.6.47.22 | 19.44.6.47.25 |
| 19.44.7.1.5 | 19.44.7.1.13 | 19.44.7.1.18 | 19.44.7.1.22 | 19.44.7.1.25 |
| 19.44.7.2.5 | 19.44.7.2.13 | 19.44.7.2.18 | 19.44.7.2.22 | 19.44.7.2.25 |
| 19.44.7.5.5 | 19.44.7.5.13 | 19.44.7.5.18 | 19.44.7.5.22 | 19.44.7.5.25 |
| 19.44.7.7.5 | 19.44.7.7.13 | 19.44.7.7.18 | 19.44.7.7.22 | 19.44.7.7.25 |
| 19.44.7.46.5 | 19.44.7.46.13 | 19.44.7.46.18 | 19.44.7.46.22 | 19.44.7.46.25 |
| 19.44.7.47.5 | 19.44.7.47.13 | 19.44.7.47.18 | 19.44.7.47.22 | 19.44.7.47.25 |
| 19.44.8.1.5 | 19.44.8.1.13 | 19.44.8.1.18 | 19.44.8.1.22 | 19.44.8.1.25 |
| 19.44.8.2.5 | 19.44.8.2.13 | 19.44.8.2.18 | 19.44.8.2.22 | 19.44.8.2.25 |
| 19.44.8.5.5 | 19.44.8.5.13 | 19.44.8.5.18 | 19.44.8.5.22 | 19.44.8.5.25 |
| 19.44.8.7.5 | 19.44.8.7.13 | 19.44.8.7.18 | 19.44.8.7.22 | 19.44.8.7.25 |
| 19.44.8.46.5 | 19.44.8.46.13 | 19.44.8.46.18 | 19.44.8.46.22 | 19.44.8.46.25 |
| 19.44.8.47.5 | 19.44.8.47.13 | 19.44.8.47.18 | 19.44.8.47.22 | 19.44.8.47.25 |
| 19.44.9.1.5 | 19.44.9.1.13 | 19.44.9.1.18 | 19.44.9.1.22 | 19.44.9.1.25 |
| 19.44.9.2.5 | 19.44.9.2.13 | 19.44.9.2.18 | 19.44.9.2.22 | 19.44.9.2.25 |
| 19.44.9.5.5 | 19.44.9.5.13 | 19.44.9.5.18 | 19.44.9.5.22 | 19.44.9.5.25 |
| 19.44.9.7.5 | 19.44.9.7.13 | 19.44.9.7.18 | 19.44.9.7.22 | 19.44.9.7.25 |
| 19.44.9.46.5 | 19.44.9.46.13 | 19.44.9.46.18 | 19.44.9.46.22 | 19.44.9.46.25 |
| 19.44.9.47.5 | 19.44.9.47.13 | 19.44.9.47.18 | 19.44.9.47.22 | 19.44.9.47.25 |
| 19.44.10.1.5 | 19.44.10.1.13 | 19.44.10.1.18 | 19.44.10.1.22 | 19.44.10.1.25 |
| 19.44.10.2.5 | 19.44.10.2.13 | 19.44.10.2.18 | 19.44.10.2.22 | 19.44.10.2.25 |
| 19.44.10.5.5 | 19.44.10.5.13 | 19.44.10.5.18 | 19.44.10.5.22 | 19.44.10.5.25 |
| 19.44.10.7.5 | 19.44.10.7.13 | 19.44.10.7.18 | 19.44.10.7.22 | 19.44.10.7.25 |
| 19.44.10.46.5 | 19.44.10.46.13 | 19.44.10.46.18 | 19.44.10.46.22 | 19.44.10.46.25 |
| 19.44.10.47.5 | 19.44.10.47.13 | 19.44.10.47.18 | 19.44.10.47.22 | 19.44.10.47.25 |

Screens for Neuraminidase Inhibitors.

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro Ki (inhibitory constants) of less then about $5\times10^{-6}$M, typically less than about $5\times10^{-7}$M and preferably less than about $5\times10^{-8}$M are excellent candidates for in vivo screening.

Useful in vitro screens have been described in detail and will not be elaborated here. However, Itzstein, M. von et al.; *Nature* 1993, 363(6428), 418–423, in particular page 420, column 2, full paragraph, to page 421, column 2, first partial paragraph, describes a suitable in vitro assay of Potier, M.; et al.; *Analyt. Biochem.* 1979, 94, 287–296, as modified by Chong, A. K. J.; et al.; *Biochem. biophys. Acta* 1991, 1077, 65–71; and Colman, P. M.; et al.; International Publication No. WO 92/06691 (Int. App. No. PCT/AU90/00501, publication date Apr. 30, 1992) page 34, line 13, to page 35, line 16, describes another useful in vitro screen.

In vivo screens have also been described in detail, see Itzstein, M. von et al.; op. cit., in particular page 421, column 2, first full paragraph, to page 423, column 2, first partial paragraph, and Colman, P. M.; et al.; op. cit. page 36, lines 1–38, describe suitable in vivo screens.

Pharmaceutical Formulations.

Another aspect of the invention relates to compositions comprising one or more pharmaceutically-acceptable carriers. One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally are coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc.), which is administered by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for inhalation therapy are prepared as aerosols or powders having a particle size small enough to dose the alveoli. Such powders and aerosols are prepared by any of the methods common in the art. Ordinarily aerosols are aqueous aerosols.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends on the nature of the condition being treated, the method of treatment, pharmaceutical formulation, and the like. It can be expected to be from about 0.001 to about 30 mg/kg body weight per day. For example, for inhalation the daily dose for an adult human of approximately 70 kg body weight will range from 1 mg to 1000 mg, preferably between 5 mg and 500 mg, and may take the form of single or multiple doses.

Active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with mucolytic, expectorant, bronchial-dilators, antibiotics, antipyretics, or analgesics. Ordinarily, antibiotics, antipyretics, and analgesics.

Methods of Inhibition of Neuraminidase.

Another aspect of the invention relates to methods of inhibiting the activity of neuraminidase comprising the step of treating a sample suspected of containing neuraminidase with a composition of the invention.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells; and the like. Typically the sample will be suspected of containing an organism which produces neuraminidase, frequently a pathogenic organism such as a virus. Samples can be contained in any medium including water and organic solvent\water mixtures. Frequent samples are living organisms such as humans, and man made materials such as bioproduct samples.

The treating step of the invention can involve adding the composition of the invention to the sample or it can involve adding a precursor of the composition to the sample. The addition step comprises any method of administration as described above.

If desired, the activity of neuraminidase after application of the composition can be observed by any method including direct and indirect methods of detecting neuraminidase activity. Quantitative, qualitative, and semiquantitative methods of determining neuraminidase activity are all contemplated. Typically one of the screening methods described above are applied, however, any other method such as observation of the physiological properties of a living organism are also applicable.

Organisms that contain neuraminidase include bacteria (Vibrio cholerae, Clostridium perfringens, Streptococcus pneumoniae, and Arthrobacter sialophilus) and viruses (influenza virus, parainfluenza virus, mumps virus, Newcastle disease virus, fowl plague virus, and sendai virus). Inhibition of neuraminidase activity related to any of these organisms is within the objects of this invention. The virology of influenza viruses is described in "Fundamental Virology" (Raven Press, New York, 1986), Chapter 24.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabeled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Immunogens, Antibodies, and Assays.

The compounds of this invention, or the biologically active substances produced from these compounds by hydrolysis or metabolism in vivo, are used as immunogens or components of immunogenic compositions to prepare antibodies capable of binding specifically to the compounds or their metabolic products which retain immunologically recognized epitopes (sites of antibody binding). The immunogenic compositions therefore are useful as intermediates in the preparation of antibodies for use in diagnostic, quality control, or the like, methods or in assays for the compounds or their novel metabolic products.

The hydrolysis products of interest include products of the hydrolysis of the protected acidic and basic groups discussed above. In preferred embodiments the acidic or basic amides comprising immunogenic polypeptides such as albumin keyhole limpet hemocyamin and others described below generally are useful as immunogens. The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results The immunogens of this invention contain the compound presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1–100, typically, 1–25, more typically 1–10 carbon atoms to the immunogenic substance. The conjugates are separated from starting materials and by products using chromatography or the like, and then are sterile filtered and vialed for storage.

The compounds of this invention include cross-linking for example through any one or more of the following groups: a hydroxyl group of X; a carboxyl group of Y; a carbon atom of E, A, B, $A_1$, or $B_1$ in substitution of H; and an amine group of Z.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ¹/₁₀ the original amount of conjugate in Freund's complete adjuvant (or other suitable adjuvant) by subcutaneous injection at multiple sites. 7 to 14 days later animals are bled and the serum is assayed for the desired antibody titer. Animals are boosted until the titer plateaus. Preferably, the animal is boosted with the conjugate in which the precursor or product is linked to a different protein, through a different cross-linking agent or both. Optionally, aggregating agents such as alum are used to enhance the immune response.

After immunization, monoclonal antibodies are prepared by recovering immune lymphoid cells (typically spleen cells or lymphocytes from lymph node tissue) from immunized animals and immortalizing the cells in conventional fashion, e.g., by fusion with myeloma cells or by Epstein-Barr virus transformation and screening for clones expressing the desired antibody. The hybridoma technique described originally be Kohler and Milstein, *Eur. J. Immunol.* (1976) 6:511 has been widely applied to produce hybrid cell lines that secrete high levels of monoclonal antibodies against many specific antigens.

It is possible to fuse cells of one species with another. However, it is preferably that the source of the immunized antibody producing cells and the myeloma be from the same species.

The hybrid cell lines are maintained in culture in vitro. The cell lines of this invention are selected or maintained in a hypoxanthine-aminopterin thymidine (HAT) medium. However, the established hybridoma cell line can be maintained on a variety of nutritionally adequate media. The secreted antibody is recovered from culture by conventional methods such as precipitation, ion exchange chromatography, affinity chromatography, or the like. The antibodies described herein are also recovered from hybridoma cell cultures by conventional methods for purification of IgG or IgM as the case may be that heretofore have been used to purify immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of test samples.

The antibodies of this invention are obtained from any animal species, but ordinarily are from murine or rat. Once a monoclonal antibody having the desired specificity and affinity is obtained, other conventional modifications of the antibodies are within the scope of this invention. For example, the complementarity determining regions of an animal antibody, together with as much of the framework domain as is needed, are substituted into an antibody of another animal species or class to produce a cross-class or cross-species chimeric antibody. Fragments or other amino acid sequence variants of monoclonal antibodies also are encompassed within the meaning of antibody as that term is used herein, for example, Fab, Fab' or (Fab')2 fragments, single chain antibodies, bi or polyspecific antibodies, and the like.

The antibodies of this invention are from any suitable class or isotype, e.g. IgG, IgM, IgA, IgD or IgE. They may or may not participate in complement binding or ADCC.

Typically, hybridomas which are capable of binding to the immunogen are screened for the ability to bind to the hapten itself in typical test samples (plasma, serum and the like) with the requisite degree of affinity. The desired affinity will depend upon the use intended for the antibody, but should be adequate to function in a conventional competitive-type ELISA or radioimmunoassays, or in conventional EMIT immunoassays.

The antibodies of this invention are used in such assays together with a labeled form of the compounds of the invention. Alternatively, the antibody is labeled. Suitable labels are well-known and include radioisotopes, enzymes, stable free radicals, fluorophors, chemiluminescent moieties and other detectable groups heretofore employed to prepare covalent conjugates for use in assays. Methods for linking the labels to ligand amino groups, or amino acid side chains or termini of polypeptides, are known and are suitable for use herein. Other suitable linking methods will be apparent to the ordinary artisan.

The antibodies and labeled ligands herein optionally are assembled into kits for use in therapeutic drug monitoring or evaluation, or for process quality control, and used in the conventional manner.

The invention also relates to methods of detecting neuraminidase in a sample suspected of containing neuraminidase comprising the steps of: treating a sample suspected of containing neuraminidase with a composition comprising a compound of the invention bound to a label; and observing the effect of the sample on the activity of the label.

Compositions of the invention include inhibitors of neuraminidase. As such the compositions will bind to locations on the surface or in a cavity of neuraminidase having a geometry unique to neuraminidase. Compositions binding neuraminidase may bind with varying degrees of reversibility. Those compounds binding substantially irreversibly are ideal candidates for use in this method of the invention. Once labeled, the substantially irreversibly binding compositions become probes for the detection of neuraminidase.

The compounds of the invention are useful for maintaining the structural integrity of glycoproteins in recombinant cell culture. Similarly, the compounds are useful for inhibiting the neuraminidase mediated or catalyzed cleavage of glycoproteins in recombinant cell culture.

Other Uses of the Compounds of the Invention.

The compounds of the invention are polyfunctional. As such they represent a unique class of monomers for the synthesis of polymers. By way of example and not limitation, the polymers could include polyamides and polyesters. Polyamides and polyesters are materials of well known utility and the present monomers provide access to polymers having unique pendent functionalities. The compounds of this invention are useful as monomers in homopolymers or comonomers with monomers which do not fall within the scope of the invention. Homopolymers of the compounds of this invention will have utility as cation exchange agents (polyesters) in the preparation of molecular sieves (polymides), textiles, fibers, films, formed articles and the like.

The preparation of polymers from the compounds of the invention is by conventional techniques. The polyesters are prepared from the compounds having a carboxylic acid as the acidic group and an alcohol or other leaving group. The polyamides are prepared from the compounds of the invention comprising an amine.

The compounds of the invention are also a unique class of polyfunctional surfactants. Particularly when the acidic group and the group comprising a basic hetero atom have a chain of 1 to 12 atoms, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms in groups X, Y, and Z. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters with a compound of the invention wherein X is an asymmetric hydroxyalkane group; 2) separating the diastereomers; and 3) hydrolyzing the ester structure. Racemic alcohols are separated by ester formation with an acid group of Y. Further, such a method can be used to resolve the compounds of the invention themselves if optically active acids or alcohols are used instead of racemic starting materials.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The incorporated reference material, together with material cited therein, contains detailed descriptions of such conditions. Typically the temperatures will be $-100°$ C. to $200°$ C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about $20°$ C.), although for metal hydride reductions frequently the temperature is reduced to $0°$ C. to $-100°$ C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

In the schemes P indicates a hydrolytically cleavable protecting group. Such groups have been described in the above cited work of Greene. Ordinarily such groups include silyl ethers, esters, amides and the like. The selection of protecting group and the need to protect a group such a hydroxyl, carboxyl, amidino, amino or the like will depend upon the order and selection of synthetic reagents and processes, considerations that will be familiar to the ordinary artisan.

The first exemplary method is set forth in Scheme 1. In the method hydroxymethylpyridine 15 is reacted with t-butyldimethylsilyl chloride in pyridine to form ether 16. Such steps are described in detail in Greene, T. W., "Protective Groups in Organic Synthesis" (John Wiley & sons, New York, 1981), pages 39–50, and in particular pages 44–46.

Compound 16 is then oxidized with m-chloroperoxybenzoic acid (m-CPBA) to form oxide 17. Such oxidations are described in Pedersen, C. L.; et al.; *ACTA Chemica Scand.*, 1970, 24, 3435.

Oxide 17 is then condensed with D-glyceraldehyde acetonide as, for example, by the method of Abramovitch, R. A.; et al.; *J. Am. Chem. Soc.*, 1967, 1537,. The acetonide is available in D-, L- and D,L- form and accordingly the absolute stereochemistry of the condensation product at position 2 of the propane triol side chain are controlled by selection of D-, L- or D,L- material.

Compound 18 is then converted to compound 19 by reaction with PhCOCl and Me$_3$SiCN. Such a reaction is described in Kobayashi, Y.; et al.; *Chem. Pharm. Bull.* (Japan), 1969, 17, 510.

Compound 19 is then converted to primary alcohol 20 by treatment with Bu$_4$NF as described in the above cited work of Greene.

Alcohol 20 is converted to the N-alkylphthalimide 21 by reaction with phthalimide, Ph$_3$P, and diethyl azodicarboxylate. This conversion is described in the above cited work of March at page 378, Mitsunobu; et al.; *J. Am. Chem. Soc.* 1972, 94, 679, Grunewald; et al.; *J. Org. Chem.* 1983, 48, 2321, and Mitsunobu, *Synthesis* 1981, 1–28.

Phthalimide 21 is then hydrolyzed to carboxylic acid 22. Such reactions are generally described in *Org. Synth.* 1955, 3, 557.

Compound 22 is then converted to compound 23 by exchange with hydrazine described in the above cited work of March at page 378 and in Ing; et al.; *J. Chem. Soc.* 1926, 2348.

A second exemplary method is shown in Scheme 2. Methyl acetoacetate 24 is condensed with (–)-2,3-O-isopropylidene-D-erythronolactone (CA reg. no. [25581-41-3]) to form dione 25. Such a transformation is described by Larock, R. C. "Comprehensive Organic Transformations" (VCH, New York, 1989), page 772. The lactone is available in D-, L- and D,L- form and accordingly the absolute stereochemistry of the condensation product side chain are controlled by selection of D-, L- or D,L- material.

Compound 25 is then reacted with H$_2$N(CCN)NH to form pyrimidine 26. Such reactions are described in Katritzky, A. R. "Handbook of Heterocyclic Chemistry" (Pergamon, New York, 1985).

Pyrimidine 26 is converted to acetate 27 by reaction with AcCl/Et$_3$N and NaI/pyridine. Such a conversion is described in Morita, T.; et al.; *J. Chem. Soc., Chem. Commun.* 1978, 874.

Acetate 27 is converted to amine 28 by reaction with ClCO$_2$Et and NAN$_3$. Such a reaction is described in Weinstock, J.; *J. Org. Chem.* 1961, 26, 3511.

Amine 28 is then converted to compound 29 by hydrolysis. Such a conversion was shown in Scheme 1.

A third exemplary method is shown in Scheme 3. Trimethyl pyridine 30 is converted to triol 31 by oxidation with KMnO$_4$ and reduction with LiAlH$_4$. Such a reaction is described in Singer, A. W.; et al.; *Org. Synth.* 1955, III, 740.

The triol is diprotected to form alcohol 32 using t-butyldimethylsilyl chloride and imidazole as described in the above cited work of Greene. Separation of the distribution of mono-, di- and tri- protected materials is accomplished in a conventional manner, typically by chromatography using silica or alumina.

MnO$_2$ oxidation of alcohol 32 produces aldehyde 33. Such an oxidation is described in Pratt, E. F.; et al.; *J. Org. Chem.* 1961, 26, 2973.

Triol 35 is prepared by reaction of aldehyde 33 with vinylmagnesium bromide and reaction of the allylic alcohol 34 with OsO$_4$/t-BuOOH. A description of the oxidation process is found in Akashi, K.; et al.; *J. Org. Chem.* 1978, 43, 2063.

Formation of the triacetate 36 and deprotection of the silyl ethers to form diol 37 is described in the above cited work of Greene.

Diol 37 is converted to the mono-N-alkylphthalimide 38 by reaction with phthalimide, Ph$_3$P, and diethyl azodicarboxylate as described above in Scheme 1. Should separation of mono- and/or di- phthalimides be required, it is performed in the usual manner, typically by silica or alumina chromatography.

Oxidation of the alcohol 38 to the carboxylic acid 39 is accomplished by traditional techniques, as for example the well known Jones reaction using $CrO_3\backslash H_2SO_4\backslash$acetone or $CrO_3\backslash HOAc\backslash H_2O$.

Deprotection of acid 39 to form amine 40 is performed using $H_2NNH_2$, as described above in Scheme 1.

A fourth exemplary method is shown in Scheme 4. Halide 41 is condensed with D-glyceraldehyde acetonide as, for example, by the method of Knight, D. W.; et al.; *Tet. Lett.* 1980, 21, 5051. As described above the acetonide is available in D-, L- and D,L- form so that the side chain stereochemistry can be selected.

The resulting acetonide 42 is protected to form compound 43. Such reactions are discussed above in Scheme 1.

Compound 43 is then converted to carboxylic acid 44 by reaction with strong base (e.g. LDA/THF) and $CO_2$. Such a reaction is described in Davies, G. M.; et al.; *Tet. Lett.* 1972, 33, 3507.

Carboxylic acid 44 is converted to nitrile 45 by reaction with $KCN/Pd(PPh_3)_4$. Such a reaction is described in Yamamura, K.; et al.; *Tet. Lett.* 1977, 50, 4429.

Nitrile 45 is then converted to compound 46 by removal of the silyl group as describe in the above cited work of Greene, and hydrogenated in a manner similar to that of Cordes, E. H.; et al.; *Chem. Rev.* 1974, 74, 5 and 581, and Rylander, "Catalytic Hydrogenation over Platinum Metals" (Academic Press, New York, 1967), pages 203–226,.

A fifth exemplary method is shown in Scheme 5. As described above in Scheme 1, Halide 41 is converted to carboxylic acid 47 which in turn is converted to acetonide 48. Compound 48 is then converted to nitrile 49 which in turn is converted to compound 50. Each of these steps was described above in Scheme 1.

A sixth exemplary method is shown in Scheme 6. Aminoacetonitrile 51 is condensed with (−)-2,3-O-isopropylidene-D-erythronolactone (CA reg. no. [25581-41-3]) to form compound 52. Such a transformation was described above in Scheme 2.

Compound 52 is extended to form compound 53 by reaction with $MeO_2CCO_2Me/Et_3N$ and $AcCl/Et_3N$ and then cyclized to form oxazole 54 by reaction with $ClCOCOCl/Et_3N$. Such a combination of transformations is described in Maeda, I.; et al.; *Bull. Chem. Soc. Jpn.* 1969, 42, 1435.

Hydrolysis of compound 55 and hydrogenation of nitrile 56 leads to compound 57. Such reactions were described in Schemes 4 and 5 above.

A seventh exemplary method is shown in Scheme 8. Commercially available methoxy acetic acid 58 and serine methyl ester 59 (Aldrich #19,455-7 and #22,313-1) is coupled using isobutyl chloroformate, 4-methyl morpholine in DMF to give amide 60. Such a conversion is described in *Tetrahedron Lett.* 1992, 33, 7835.

Alcohol 60 is converted to the vinyl bromide in four steps as described in *Tetrahedron Lett.* 1992, 33, 7835.

Vinyl bromide 61 is converted into the 5-bromo oxazole 62 by treatment with $CuBr_2$ and DBU in $CH_2Cl_2$ as described in *Tetrahedron Lett.* 1992, 33, 7835.

Methyl ester 62 is reduced with diisobutylaluminum hydride to the corresponding aldehyde and then converted to the primary amine by reductive amination using ammonia and $NaBH_3CN$. Such a conversion is described in *Synthesis* 1975, 135.

Amine 63 is protected with phthaloyl dichloride to give phthalimide 64 as described in the above cited book of Greene.

Methyl ether 64 is cleaved with TMS iodide as described in *J. Org. Chem.* 1977, 42, 3761. Subsequent oxidation gives the carboxylic acid 65. Such conversions are described in the above cited book of LaRock.

5-Bromo oxazole 65 is converted to the 5-lithio derivative with n-butyllithium. Such a conversion is described in *Tetrahedron* 1968, 24, 3965. The anion is condensed with either D- or L- glyceraldehyde acetonide to give 66. D- or L- glyceraldehyde is obtained according to the references cited earlier.

Removal of the amine protecting group of 66 according to the methods cited in Greene followed by subsequent hydrolysis of the acetonide with TsOH/MeOH gives the triol 67. Such a conversion is described in *Tetrahedron Lett.* 1977, 3473.

An eighth exemplary method is shown in Scheme 8. 5-bromo oxazole 64 is converted into the 5-lithio derivative as described in the above conversion of 65. Trapping with $CO_2$ gas gives the corresponding carboxylic acid. Such a conversion is described in *Tetrahedron Lett.* 1975, 3973. Cyclization of the amine and carboxylic acid gives the lactam 68. Such conversions are described in the cited book of LaRock, pg. 944.

Methyl ether 68 is cleaved as described above for 64 followed by subsequent oxidation with PDC and addition of vinyl lithium gives the allylic alcohol 69.

Sharpless epoxidation of 69 followed by opening of the epoxide gives the triol 70. Such conversions are described in *J. Am. Chem. Soc.* 1973, 95, 6136 and *Synthesis* 1981, 280.

Cleavage of the lactam 70 gives the corresponding free amino carboxylic acid 71.

A ninth exemplary method is shown in Scheme 9. Compound 62 is reduced with diisobutylaluminum hydride and the resultant alcohol protected with t-butyldiphenylsilyl chloride to give the silyl ether 72. Such conversions are described in *Synthesis* 1975, 617 and *Can J. Chem.* 1977, 55, 562.

Vinyl bromide 72 is converted in several steps to the primary amine 73 by treatment with n-butyllithium and DMF. Such a conversion is described in *J. Org. Chem.* 1991, 56, 449. Reductive amination, as described previously in the transformation of 62 into 63 gives the amine 73.

Silyl ether 74 is treated with TBAF and then oxidized to the corresponding carboxylic acid which is cyclized to give lactam 74. Such conversions are described in the above cited book of LaRock, pg. 944.

Compound 74 is treated with TMS iodide and oxidized to the aldehyde 75 with PCC. Such a conversion is described in *Tetrahedron Lett.* 1975, 2647.

Compound 75 is converted into the triol 76 by the same method as described for the conversion of 69 into 70.

Cleavage of lactam 76 gives the free amino carboxylic acid 77.

A tenth exemplary method is shown in Scheme 10. 1,3-Diketone 90 is condensed with carbohydrate derived 91 in the presence of $NH_3$ to afford pyrimidine 92. Such general synthetic methods are described in "Comprehensive Heterocyclic Chemistry" Boulton, A. J.; McKillop, A., eds. (Pergamon, New York, 1984), v. 3. p. 106.

Monosaponification of 92 using standard conditions (NaOH or $Ba(OH)2/MeOH$) followed by conversion of the resulting carboxylic acid to the amide ($SOCl_2$ then $NH_3$) provides amide 93.

Treatment of 93 under dehydrative conditions affords nitrile 94. Such a conversion is described by Yamamoto; Tetrahedron Lett. 1970, 4843.

Compound 94 is then subjected to basic hydrolysis (*Org. Synth.* 1963, 4, 608) with subsequent catalytic hydrogenation of the nitrile functionality, as described in Scheme 4, affording the corresponding functionalized pyrimidine 95.

An eleventh exemplary method is shown in Scheme 11. 2,6-Dimethyl pyridine 96 is converted under oxidative conditions to the diacid, which is then esterified to the diester 97. Such general manipulations are described in "Pyridine and its Derivatives", Supplement, Abramovitch, R. A. ed. (John Wiley, New York, 1974). vol 1–5 and "Comprehensive Heterocyclic Chemistry" Boulton, A. J.; McKillop, A., eds. (Pergamon, New York, 1984), v. 2.

Reduction of 97 with DIBAL gives aldehyde 98. Such a conversion is described in Tetrahedron Lett. 1962, 619 and 1969, 1779.

Addition of vinyl magnesium bromide to aldehyde 98 followed by further functionalization of the double bond with either $OsO_4$ or epoxidation/basic hydrolysis then provides triol 99. Such a process has been described in Scheme 3.

Treatment of 99 with an excess of benzoyl chloride and base, results in protection of the hydroxyl groups and conversion of the pyridine to its pyridinium salt. Addition of cyanide to the pyridinium salt affords nitrile 100. Such addition of nucleophiles to pyridinium salts has been described in "Pyridine and its Derivatives" ed. Supplement, Abramovitch, R. A. ed. (John Wiley, New York, 1974). vol 1–5.

Basic hydrolysis of 100, under standard conditions, removes both ester and alcohol protecting groups. The carboxylic acid-triol intermediate is then subjected to catalytic hydrogenation affording functionalized pyridine 101. Such a reductive process was described in Scheme 4.

A twelfth exemplary method is shown in Scheme 12. 1-Carboxy-2,6-dihydroxypyridine 102 was reacted with $POBr_3$ at 170° C. to produce 1-carboxy-2,6-dibromopyridine 103 which was then converted to the N-acytyl compound 104 by sequential reaction with $SOCl_2$, $NH_3 \cdot H_2O$, $BH_3 \cdot THF$, and $Ac_2O$/pyridine. Conversion to allylic alcohol 105 was accomplished using $Pd(PPh_3)_4$ in toluene at 100° C. Compound 105 was reacted with $CO/EtOH/Et_3N$ using $PdCl_2(PPh_3)_2$ as a catalyst at 100° C. and 120 psi to produce ester 106. Oxidation to the triol 107 was accomplished using $OsO_4/K_3Fe(CN)_6$ in t-$BuOH/H_2O$. Hydrolysis using NaOH/ $EtOH/H_2O$ at 90° C. followed by acidification with HCl produced triol 108. Conversion of 108 to 109 was accomplished in 10% $KHCO_3$.

A thirteenth exemplary method is shown in Scheme 13. Compound 105, prepared above, is reacted with $HPO(OEt)_2$ using $Pd(PPh_3)_4$ as a catalyst at 90° C. by the method of Hirao, T.; Masunaga, T.; Yamada, N.; *Bull. Chem. Soc. Japan,* 1982, 55, 909, to produce allylic alcohol 110. Compound 110 is reacted with $OsO_4/K_3Fe(CN)_6$ in t-$BuOH/H_2O$ to prepare triol 111. Deprotection with TMSBr produces compound 112 which is converted to disalt 113 by use of $NaOH/MeOH/H_2O$. Guanidine 114 is prepared in 10% $KHCO_3$.

A fourteenth exemplary method is shown in Scheme 14. Amine salt 115 was converted to acetate 116 by use of AcCl in pyridine. Compound 116 was reacted with allyl bromide ($CH_2CHCH_2Br$) at 55° C. in $DMF/K_2CO_3$ to form allyl ether 117. Rearrangement to form phenol 118 was performed in diethylaniline at 200° C. Protection was accomplished with PhC(O)Cl in pyridine to form compound 119 which was oxidized with $OsO_4$ in N-methylmorphiline oxide to diol 120. Deprotection was performed with NaOH in $H_2O/EtOH$ to form free phenol 121 which was converted to guanidine 122 in 10% $KHCO_3$.

A fifteenth exemplary method is shown in Scheme 15. Phenol 123 is protected by sequential treatment with MeOH/ $H_2SO_4$ and AcCl/pyridine to form phenol 124. Conversion to allyl ether 125 is accomplished by treatment with allyl bromide in $K_2CO_3$. Rearrangement in xylene at 190° C. produces phenol 126. Sequential treatment of compound 126 with $MeI/K_2CO_3$, $OsO_4$/N-methylmorphiline oxide, and $Ac_2O$/pyridine produces fully protected compound 127. Reaction with $[F_3CC(O)]_2O/NH_4NO_3$ produces protected nitro phenol 128. Deprotection with $Br_3$ produces nitro phenol 129. Hydrogenation to amine 130 is accomplished using $H_2$/Pd—C. Hydrolysis with NaOH in $H_2O$/MeOH produces diol 131 which is converted to guanidine compound 132 by reaction with $(BocNH)_2C(S)$ followed by $F_3CCO_2H$.

A sixteenth exemplary method is shown in Scheme 16. Phenol 126 (prepared above) is reacted sequentially with $C_6H_5N(SO_2CF_3)_2$ and $Pd(OAc)_2/PPh_3/Et_3N/HCO_2H$ to produce ester 133. Oxidation with $OsO_4$/N-methyl morphiline oxide followed by $Ac_2O$/pyridine produces protected diol 134. Reaction of compound 134 with $(F_3C(O))_2O$ and $NH_4NO_3$ produces compound 135 which is hydrogenated using $H_2$/Pd—C to form amine 136. Hydrolysis with NaOH in $H_2O$/MeOH forms diol 137, which is converted to guanidine 138 by sequential reaction with $(BocNH)_2C(S)$ followed by $F_3CCO_2H$.

A seventeenth exemplary method is shown in Scheme 17. Diamine 139 is reacted with HCl in MeOH to form ester 140. Reaction with $(BocNH)_2C(S)$ in $Et_3N$ in DMF using $HgCl_2$ produces compound 141. Treatment with $Ac_2O$ in pyridine using DMAP produces 142 which in turn is converted to acid 143 using LiOH followed by TFA.

A eighteenth exemplary method is shown in Scheme 18. Phenol 144 is reacted with HCl in MeOH to form ester 145. Reaction with $Ac_2O$ in pyridine produces compound 146 which is nitrated by reaction with $H_2SO_4$ in $HNO_3$ to form compound 147. Hydrogenation using $H_2$/Pd/C produces amine 148. Amine 148 is reacted with $(BocNH)_2C(S)$ in $Et_3N$ in DMF using $HgCl_2$ to produce compound 149 which in turn is converted to acid 150 using LiOH followed by TFA.

A ninteenth exemplary method is shown in Scheme 19. Compound 142 is brominated with pyridinium bromide perbromide to form compound 151. Substitution using tetravinyltin/Pd produces vinyl compound 152. Oxidation with $OsO_4$ in N-methylmorpholine oxide produces diol 153 which in turn is converted to acid 154 using LiOH followed by TFA.

Modifications of each of the above schemes leads to various analogs of the specific exemplary materials produced above. The above cited citations describing suitable methods of organic synthesis are applicable to such modifications. By way of example, and not limitation, a number of specific modifications will be described. The specific modifications are applicable to other compounds having similar functional groups including other specifically disclosed compounds. In each of these exemplary modifications, it may be appropriate to prepare protected derivatives of the starting materials as described in the above cited work of Greene. Generally, protection is not required, however, to optimize yields and reduce separation and purification steps to a minimum, protection may be advantageous. In certain individual cases prior protection of starting materials may have a significant effect on yield or purity.

The acidic substituent of the compounds prepared in Schemes 1 and 2, the basic substituent of the compounds prepared in Schemes 4, 5, and 6, and either substituent in the compound prepared in Scheme 3, are produced by way of a nitrile intermediate (compounds 21, 28, 45, 49, and 56). Any of these substituents can be produced in homologous form by conversion of the nitrile first to an aldehyde, homologation of the aldehyde by the desired number of carbon atoms and conversion of the product to a carboxylic acid (or other acidic function) or amine (or other basic hetero atom containing function). The conversion of the nitrile to the aldehyde is accomplished by reaction of the nitrile with (i-Bu)$_2$AlH in benzene. Such a conversion is described in *Org. Chem.* 1959, 607, 627. The direct homologation of an aldehyde can be performed by wittig reaction with an appropriate reagent. The aldehyde is reacted with Ph$_3$P=CHSPh (or homologous reagent)/Me$_2$SO and HgCl$_2$/HgO/H$_2$O to produce the homolog. Such a conversion is described in *Tetr. Lett.* 1969, 3665.

The carboxylic acid group of compounds 23, 29, 39, 46, 50, and 57 can be homologated by conversion of the corresponding ester to the aldehyde and applying the above described method for aldehyde homologation. The ester is reacted with (i-Bu)$_2$AlH/toluene/hexane/Et$_2$O to produce the aldehyde. Such a conversion is described in *Tetr. Lett.* 1962, 619, and 1969, 1779.

Compounds 18, 25–27, 32, 38, 49, 52, and 55 are all primary or secondary mono-ols. As such each can be homologated by oxidation to the corresponding aldehyde or ketone by standard techniques. The carbonyl compound is then homologated by reaction with Ph$_3$P=CHSPh (or homologous reagent)/Me$_2$SO and HgCl$_2$/HgO/H$_2$O. Such a conversion is described in *Tetr. Lett.* 1969, 3665. Once homologated the material can be reduced by standard techniques to the homologated alcohol.

The sulfur analogs of the carboxylic acid compounds of the invention are prepared by any of the standard techniques. By way of example and not limitation, the acids are reduced to the alcohols by standard methods. The alcohols are converted to halides or sulfonic acid esters by standard methods and the resulting compounds are reacted with NaSH to produce the sulfide product. Such reactions are described in Patai, "The Chemistry of the Thiol Group" (John Wiley, New York, 1974), pt. 2, and in particular pages 721–735.

In addition to the modification reactions described above, each of the synthetic methods of the invention produce modified products when different starting materials are employed. By why of example and not limitation, methylated analogs of compounds 15, 24, 27, 30, and 41 are all available and can be readily substituted.

Acids and amines of the Y and Z groups are modified to form amides. For example, a carboxylic acid or amine group is reacted with an amino acid or polypeptide to form an amide. Alternatively, the carboxylic acid component can be readily activated by any of the techniques common in polypeptide synthesis to form an activated carboxylic acid and then reacted with an amine. Amines are converted to form mono- and di-alkyl amines by the standard methods of amine alkylation.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involve treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Each of the cited works above is incorporated by reference in its entirety. Specifically cited sections or pages of the above cited works are incorporated by reference with specificity. The invention has been described in detail sufficient to allow one of ordinary skill in the art to make and use the subject matter of the following claims. It is obvious that certain modifications of the methods and compositions of the following claims can be made within the scope and spirit of the invention.

Scheme 1

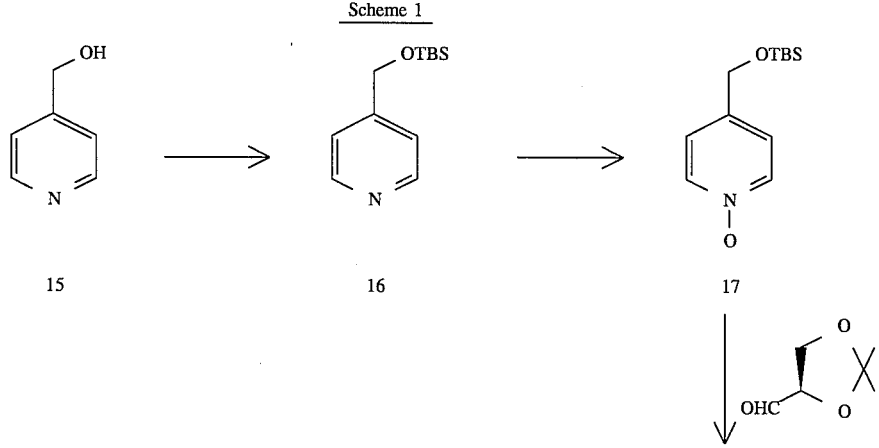

5,512,596
41 42
-continued
Scheme 1
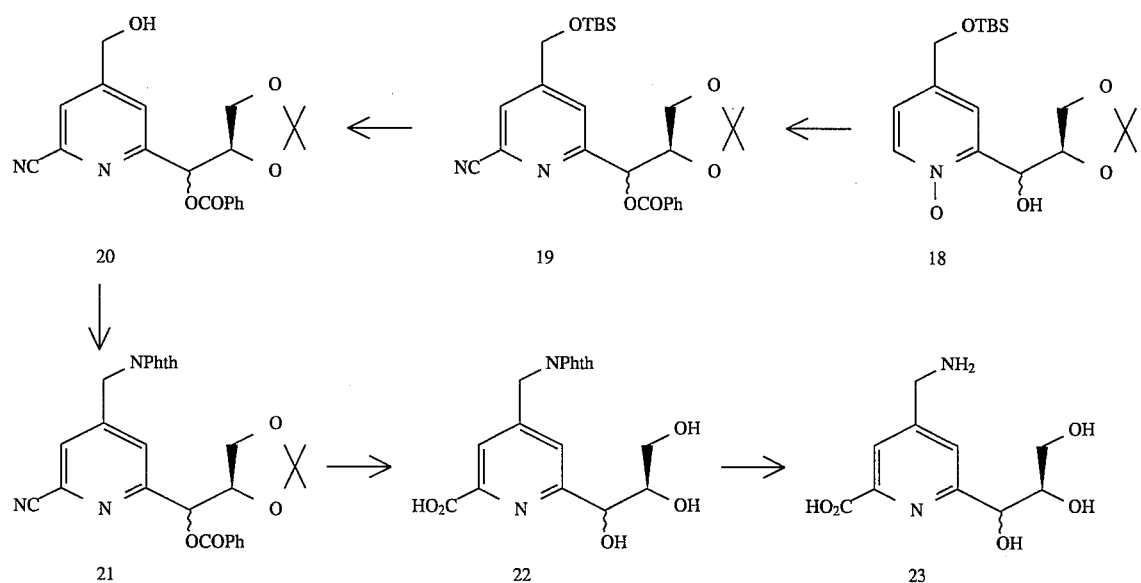
Scheme 2
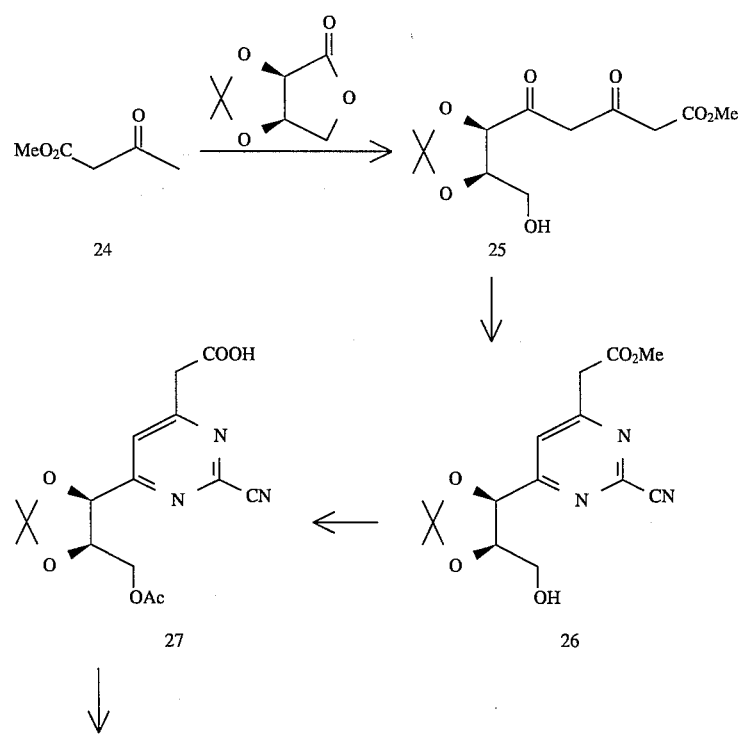

-continued
Scheme 2
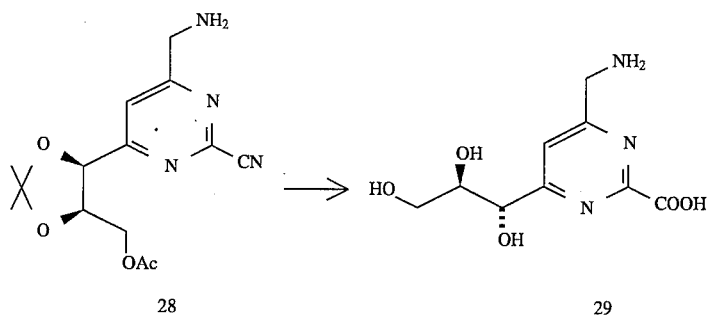
Scheme 3
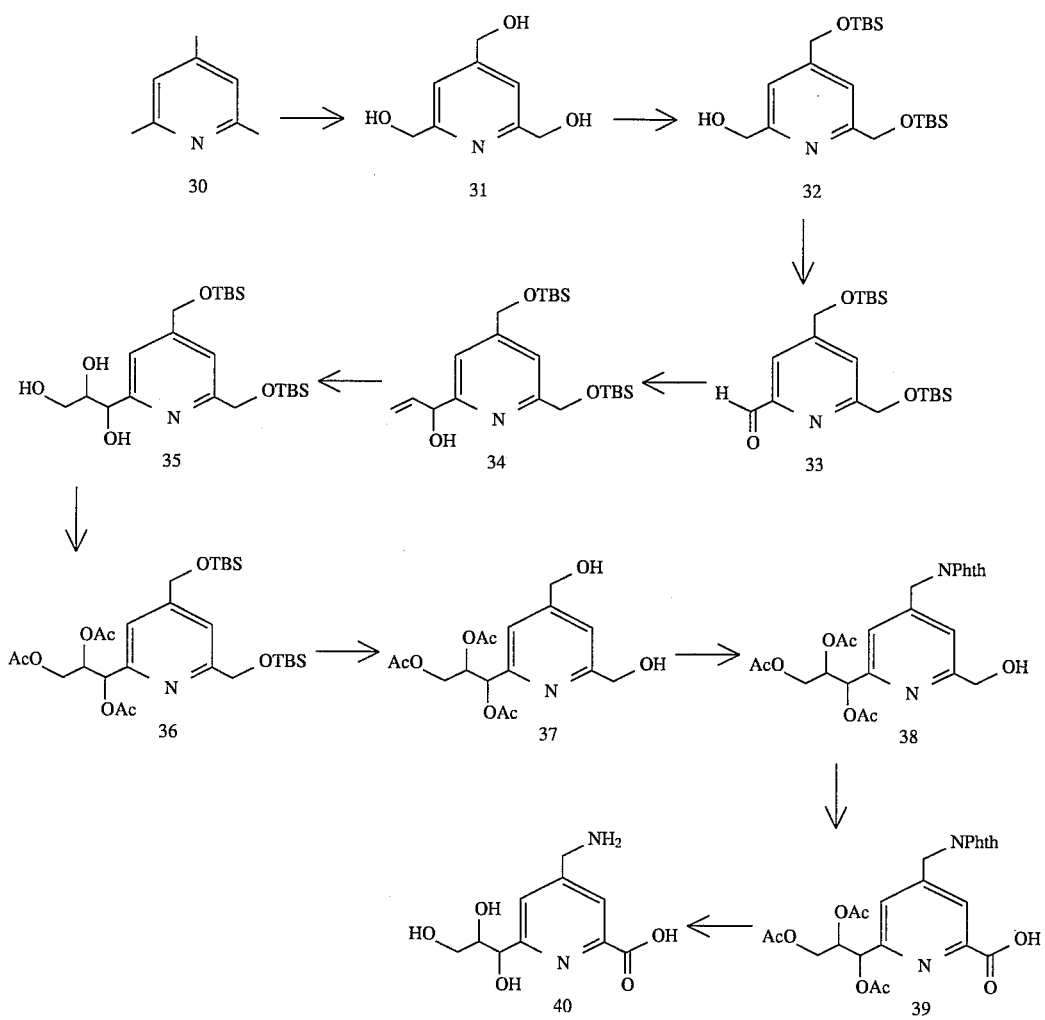

Scheme 4
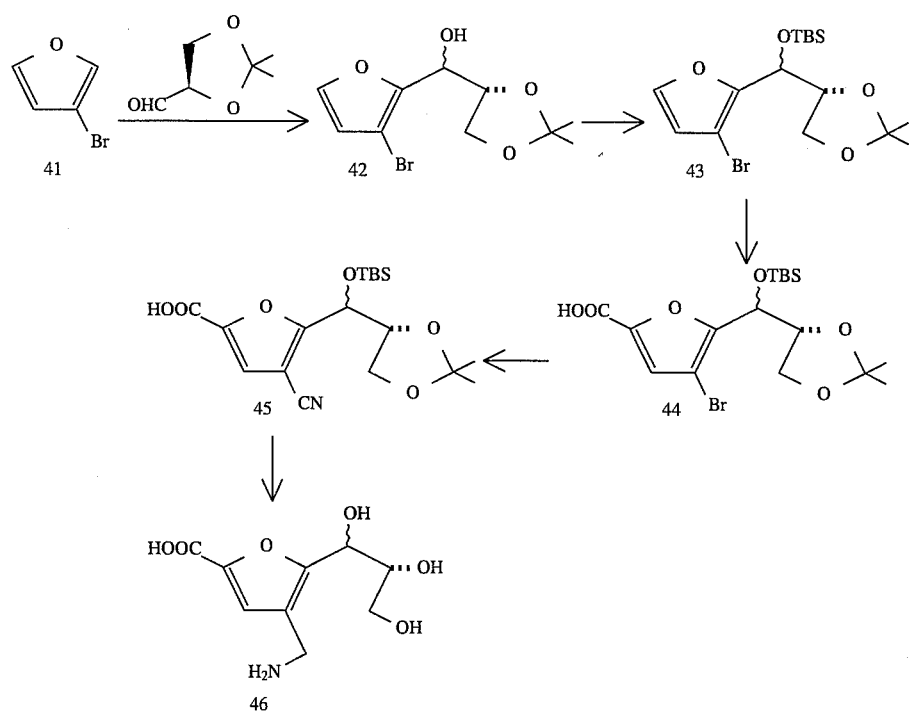
Scheme 5
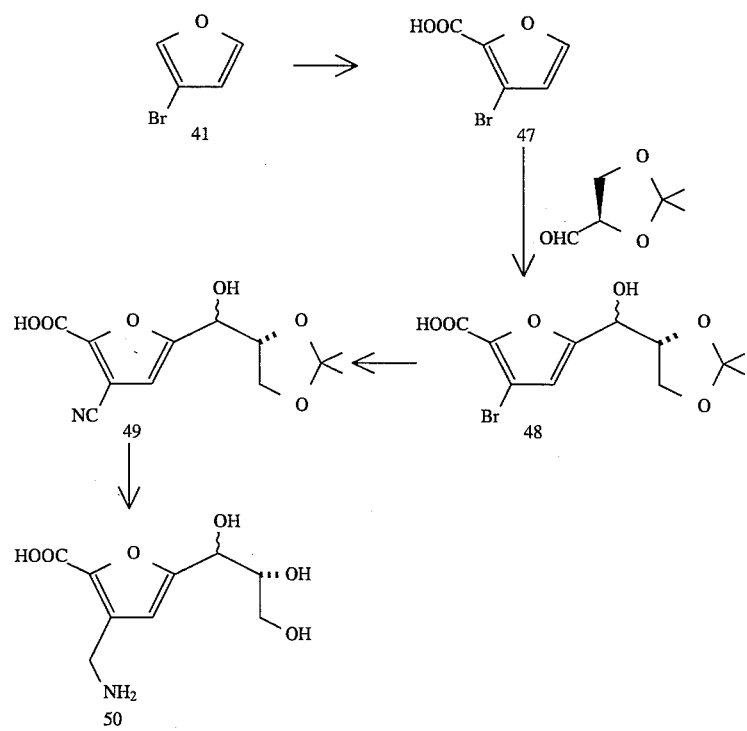

Scheme 6
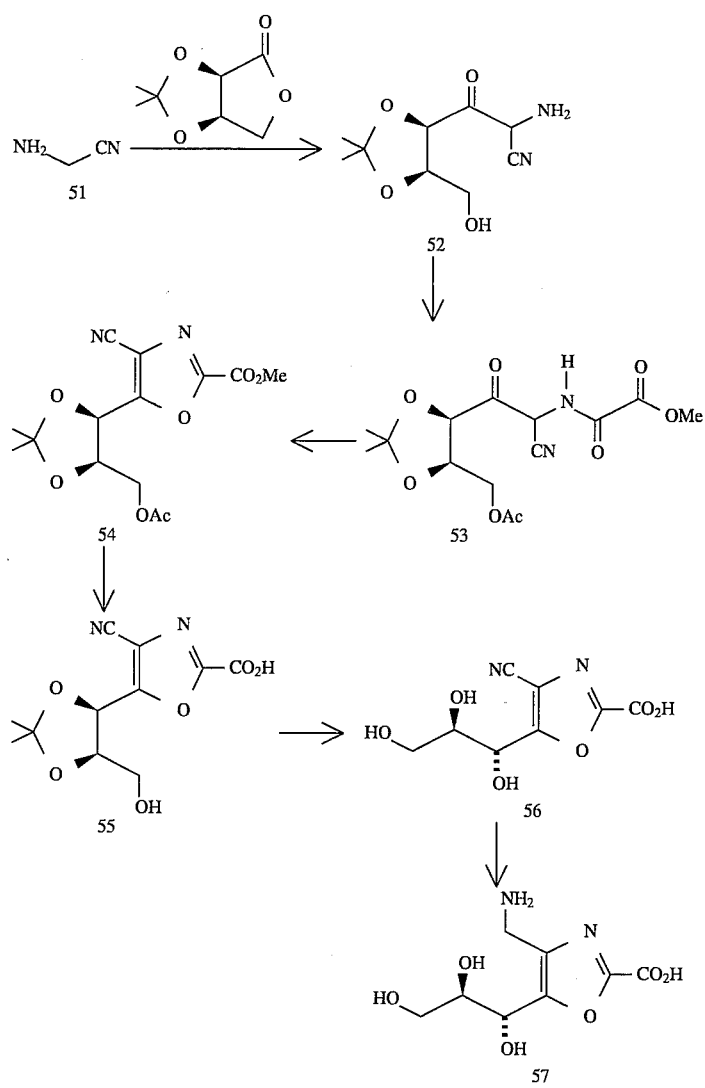
Scheme 7
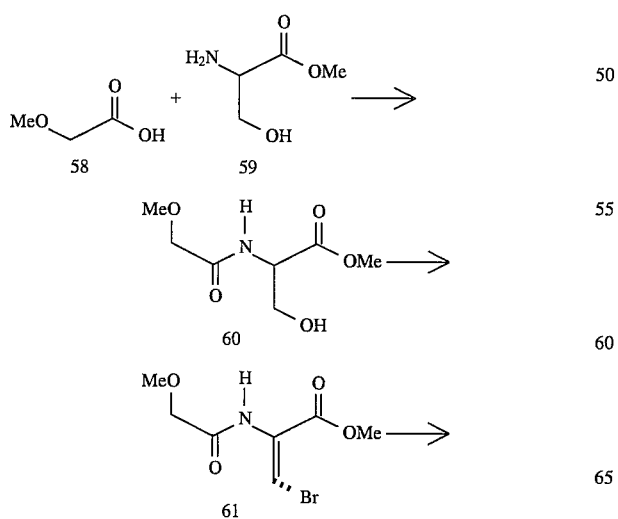
-continued
Scheme 7
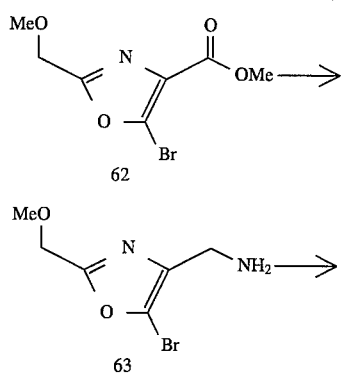

49
-continued
Scheme 7
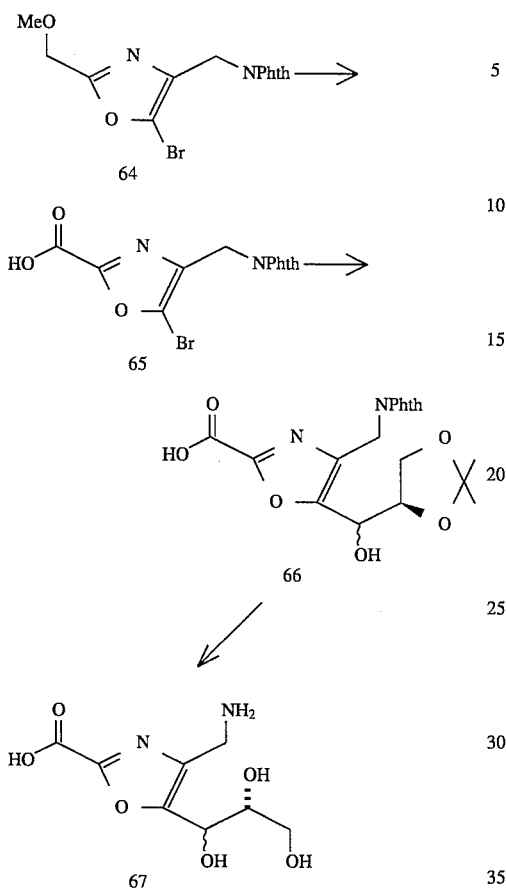
Scheme 8
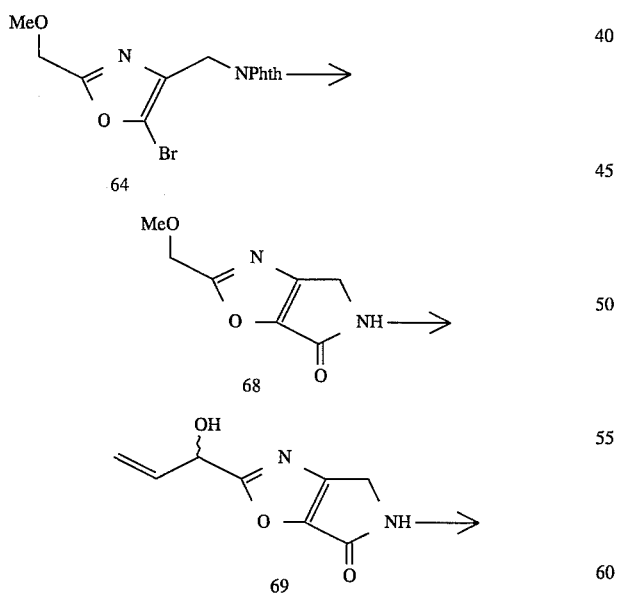
50
-continued
Scheme 8
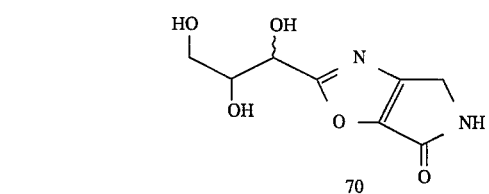
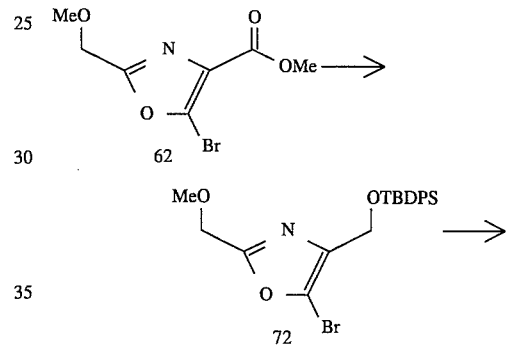
Scheme 9
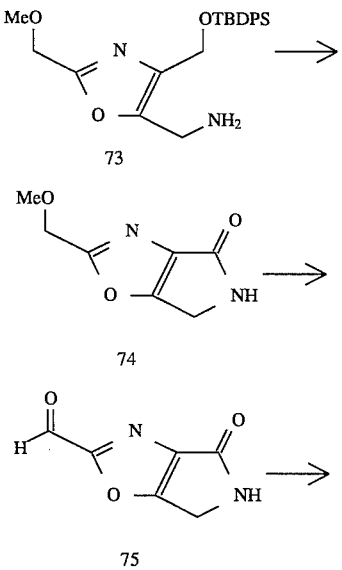

Scheme 9 -continued
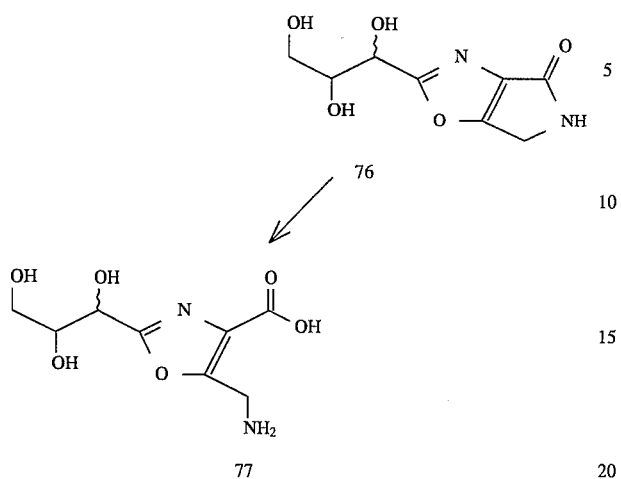
Scheme 10
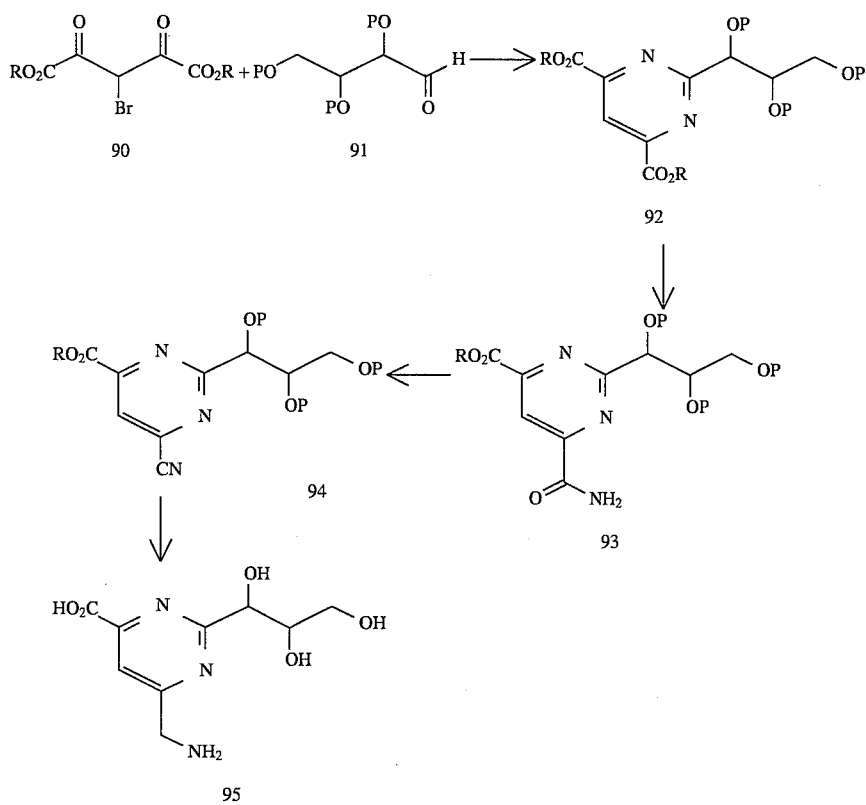

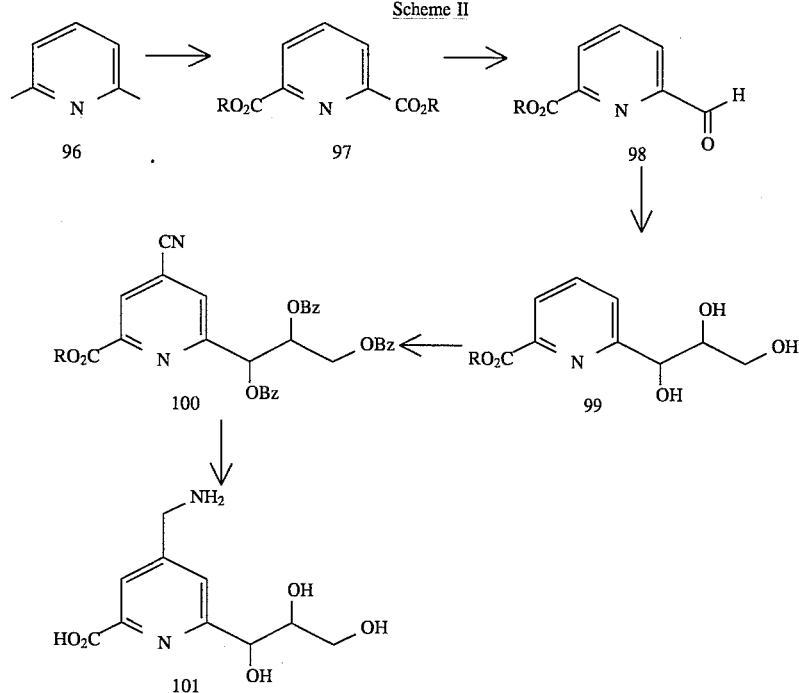
Scheme II
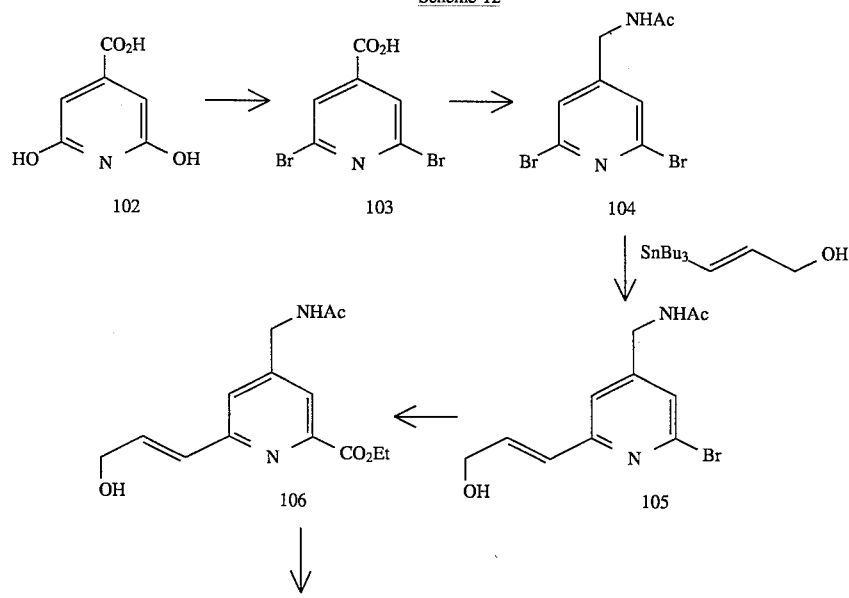
Scheme 12

-continued
Scheme 12
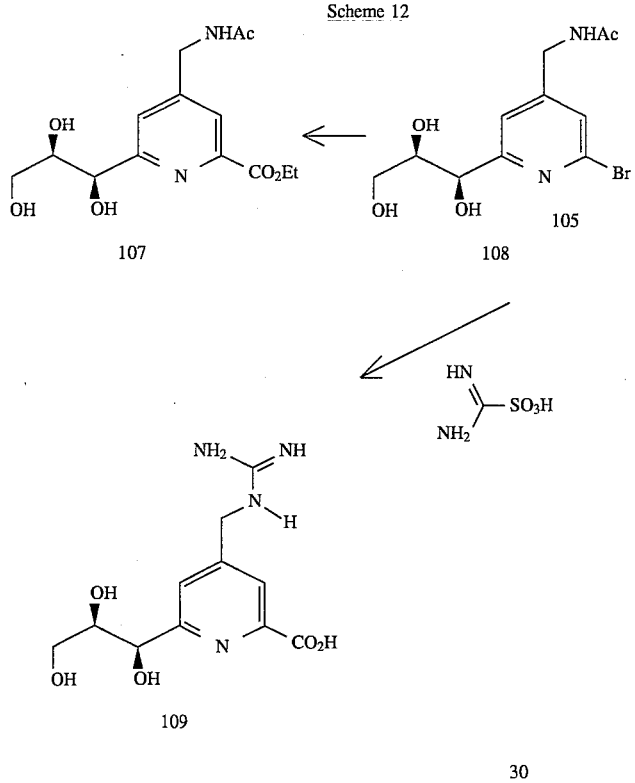
Scheme 13
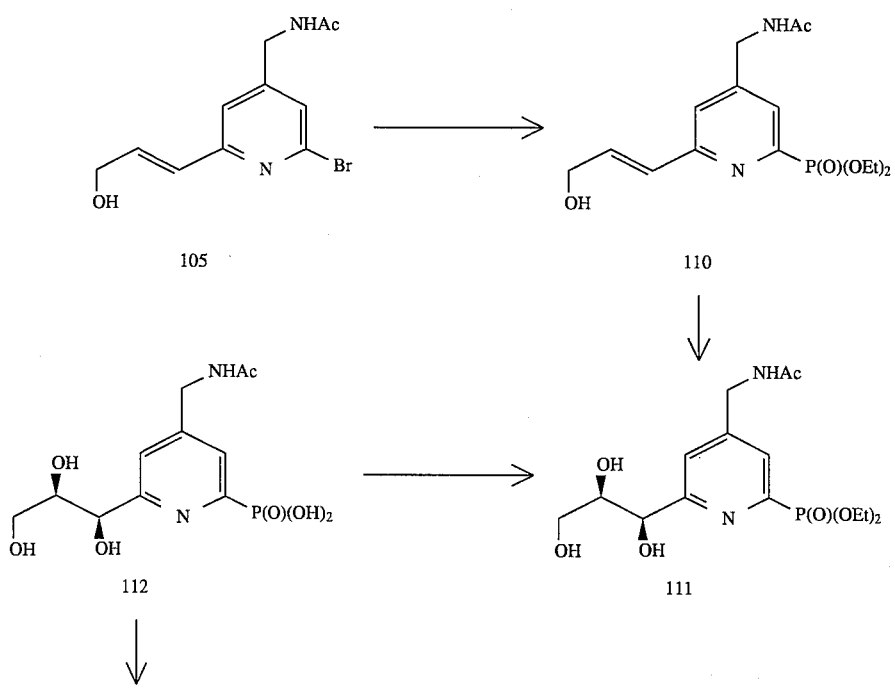

-continued
Scheme 13
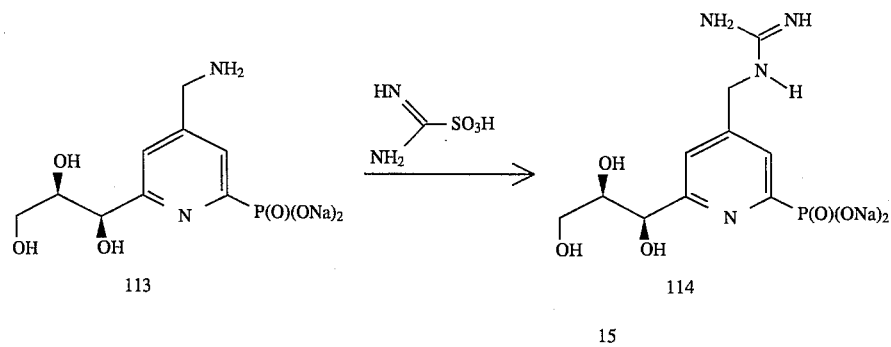
Scheme 14
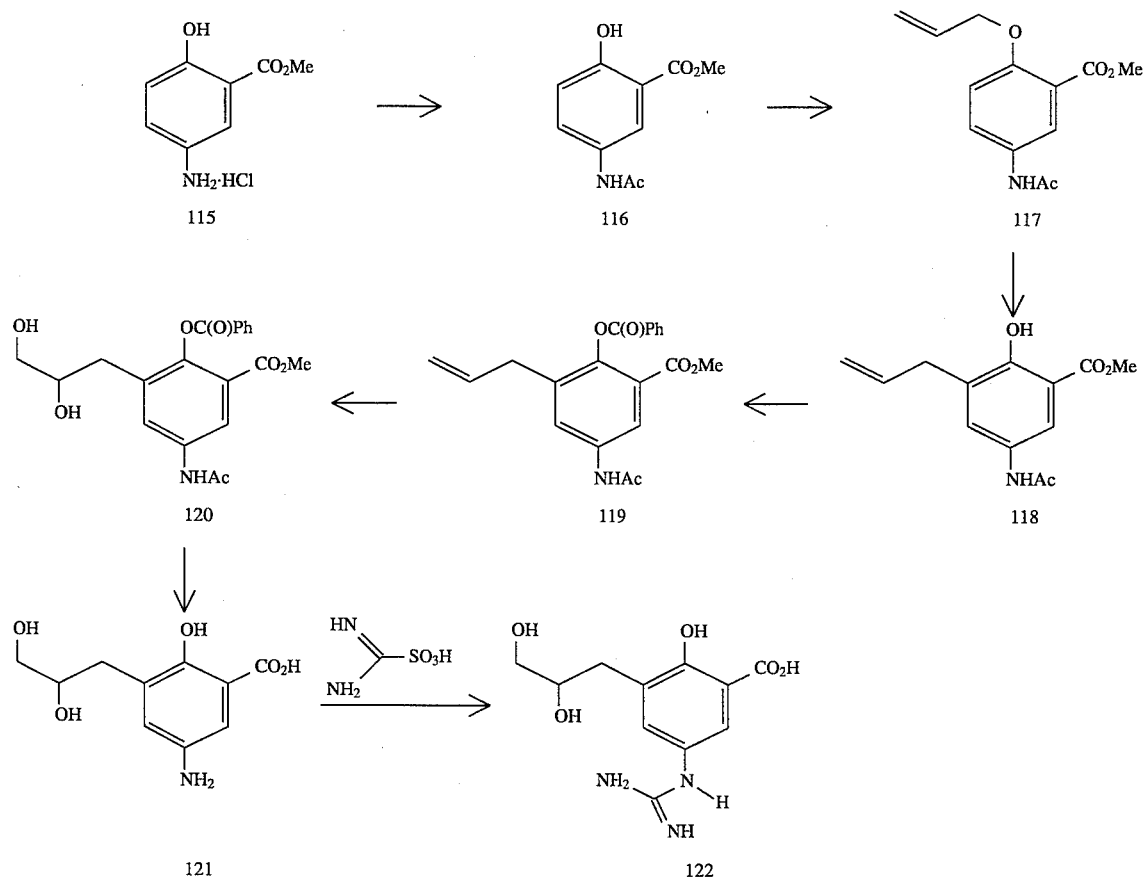

Scheme 15
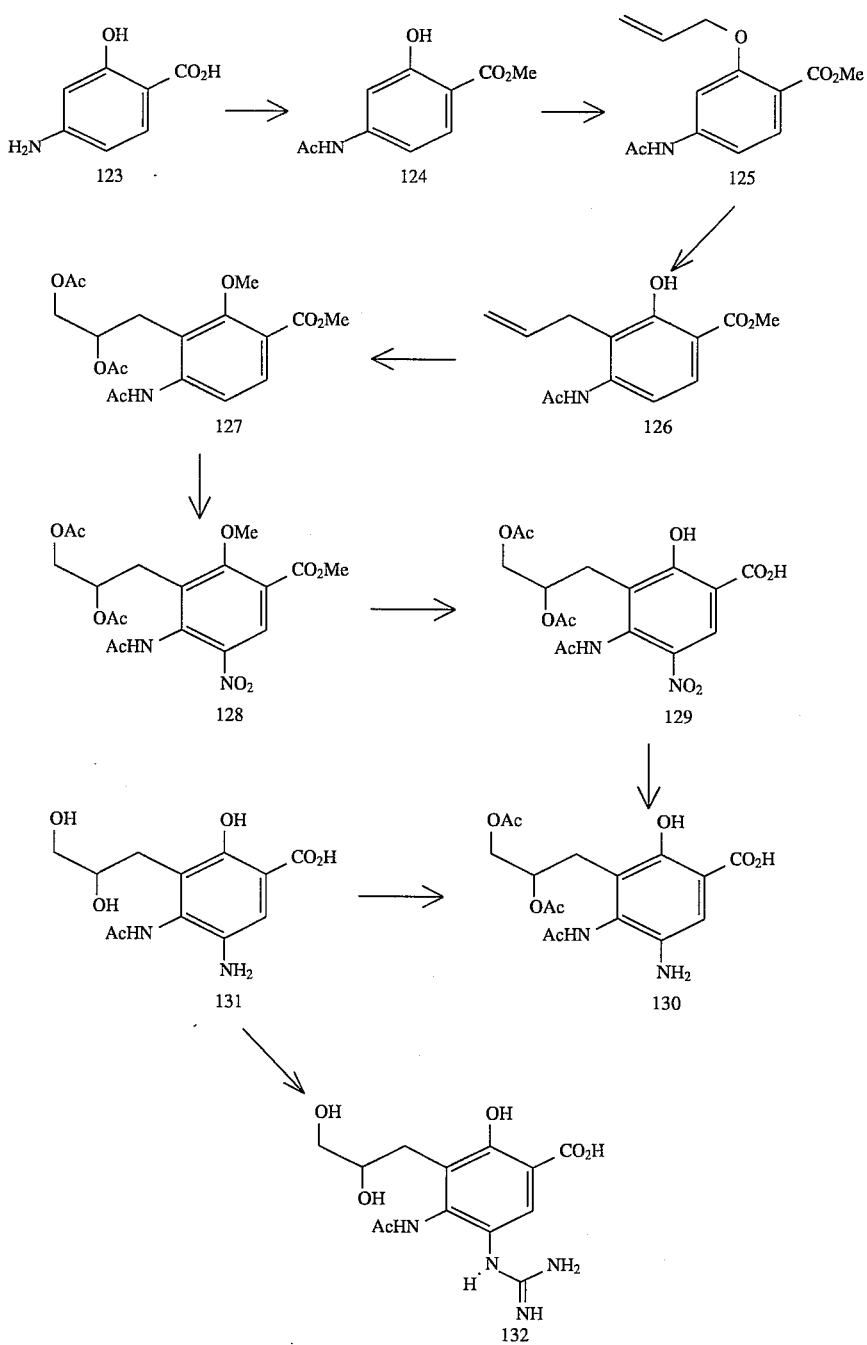

5,512,596
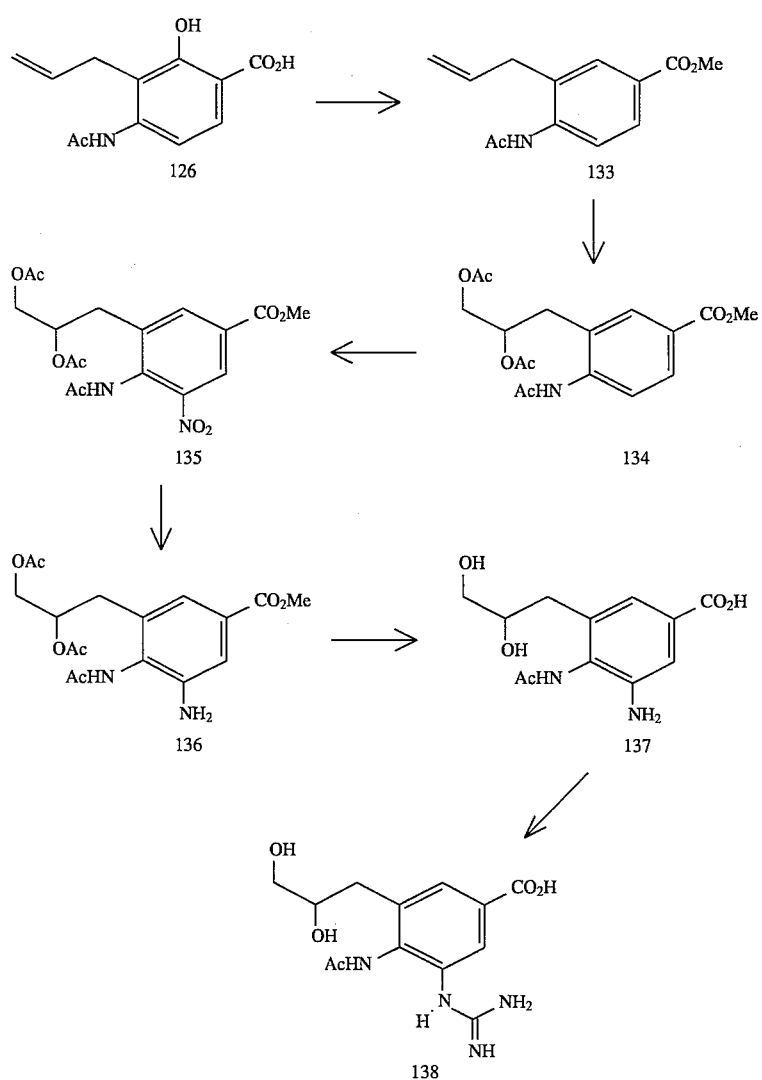
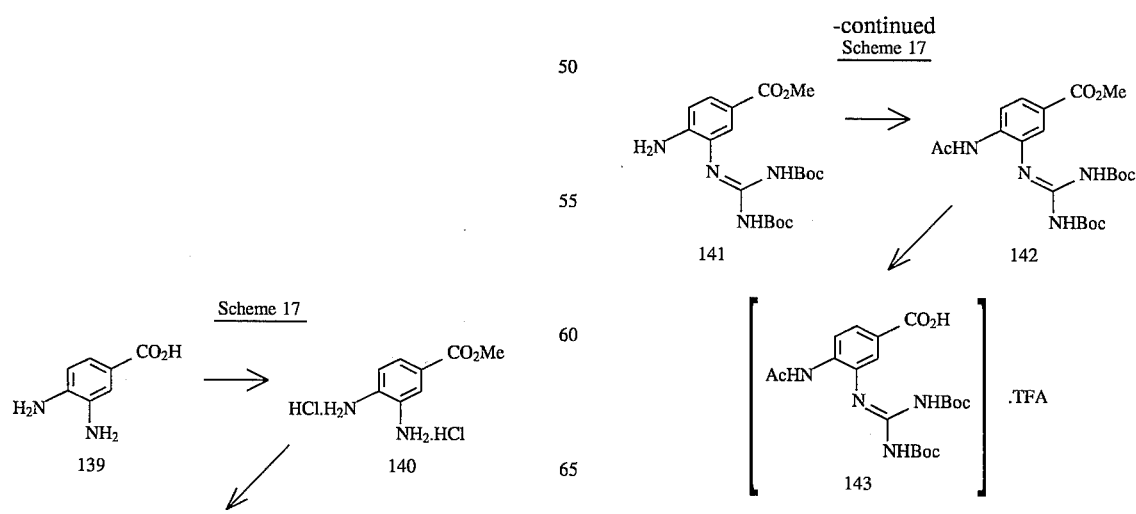

5,512,596
63
Scheme 18
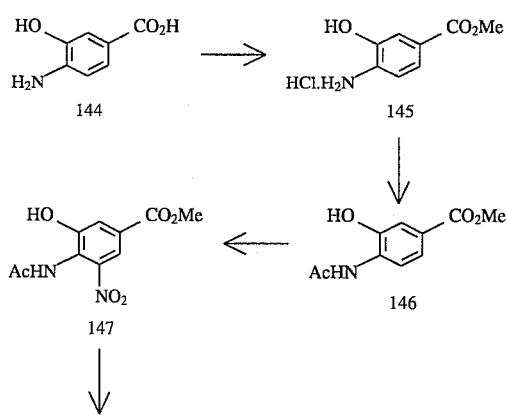
64
-continued
Scheme 18
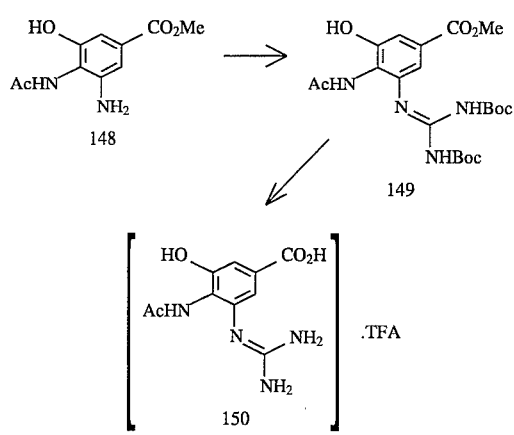
Scheme 19

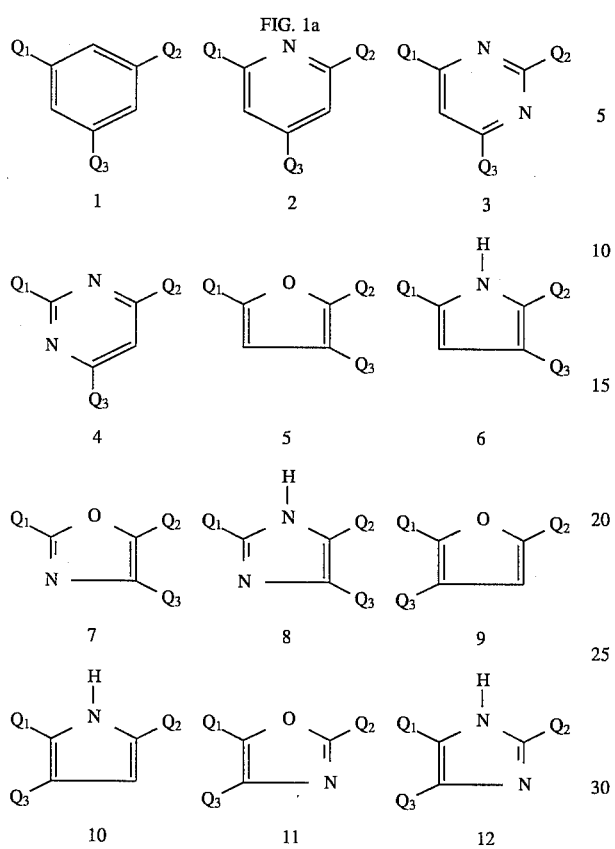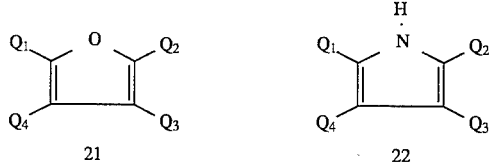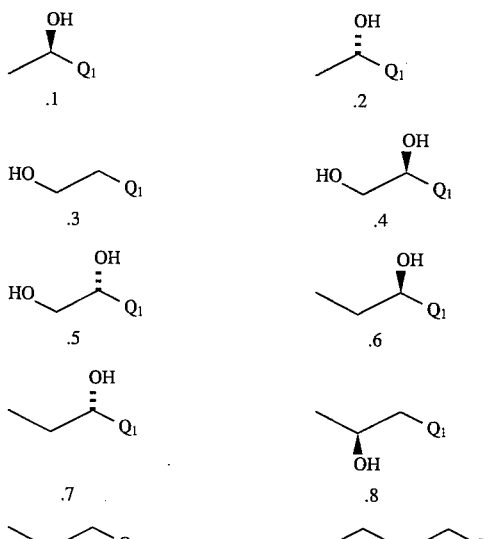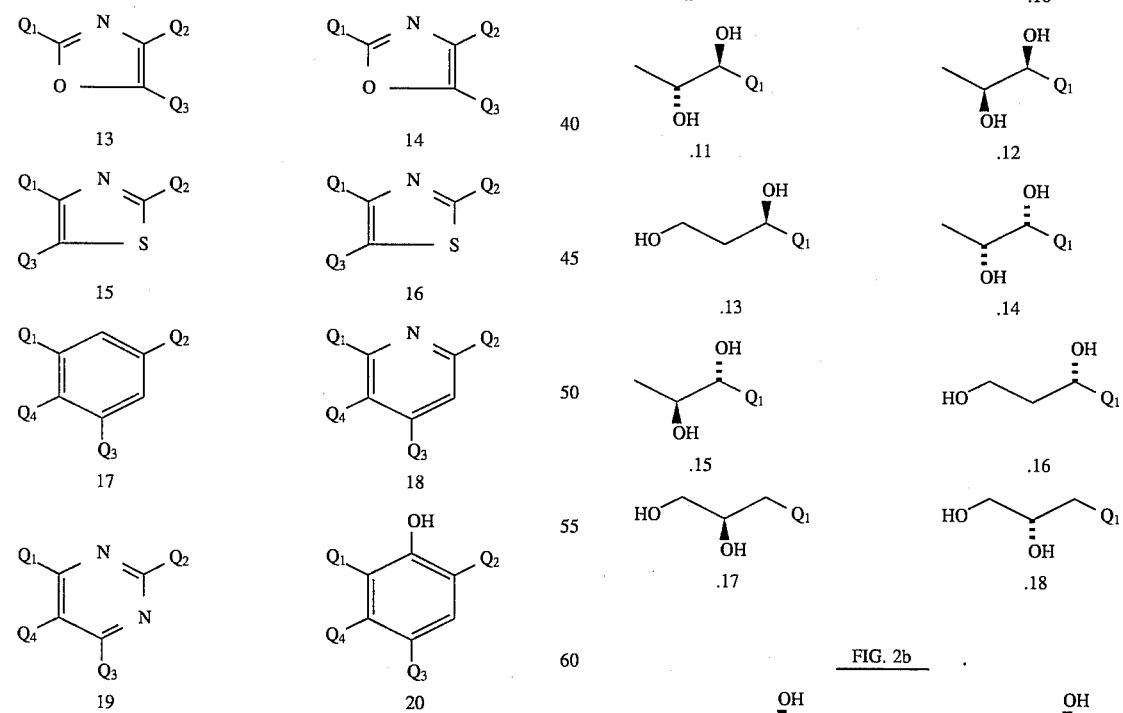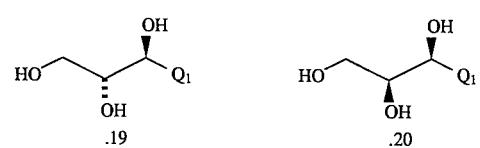

-continued
FIG. 2b
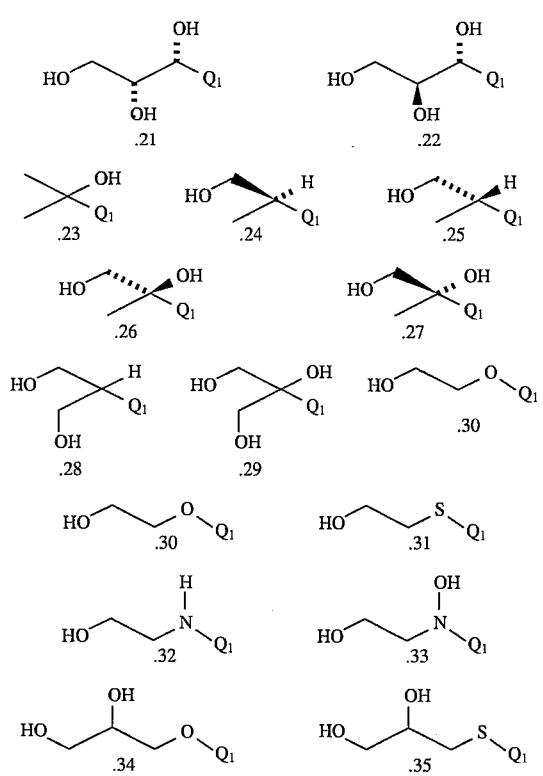
FIG. 2c
FIG. 3
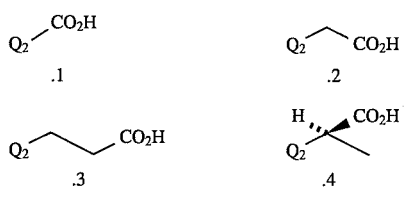
-continued
FIG. 3
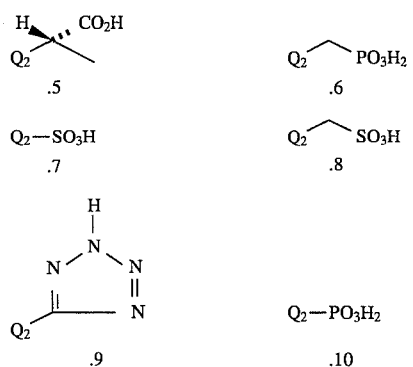
FIG. 4a
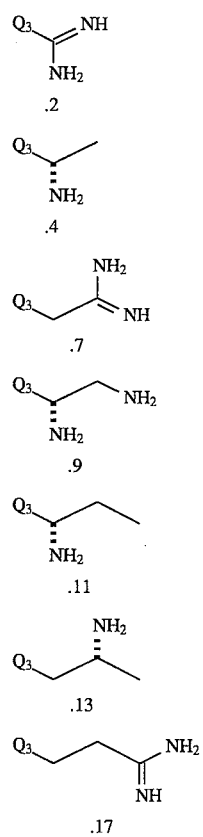
FIG. 4b
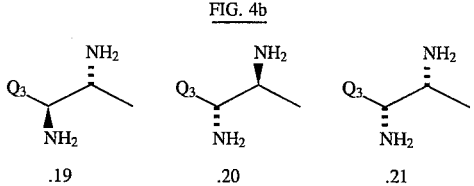

-continued
FIG. 4b
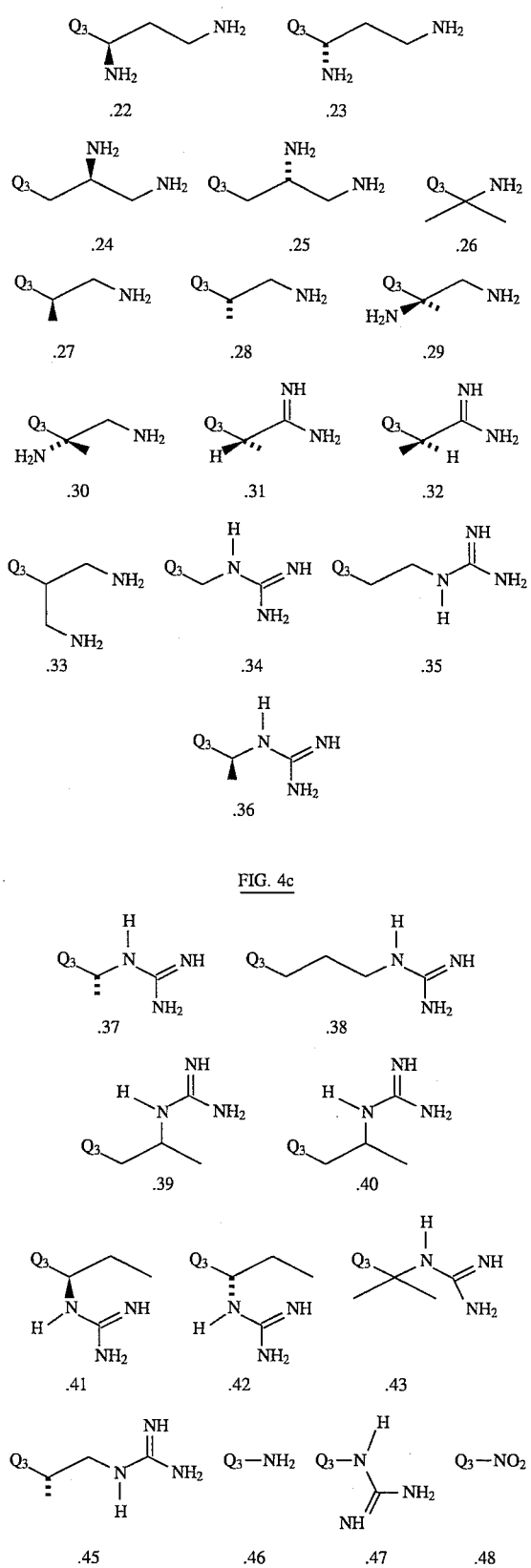
FIG. 5a
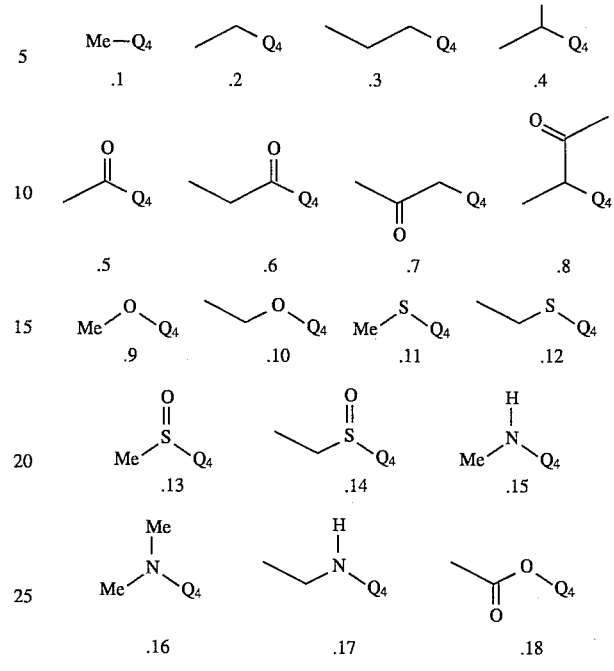
FIG. 5b
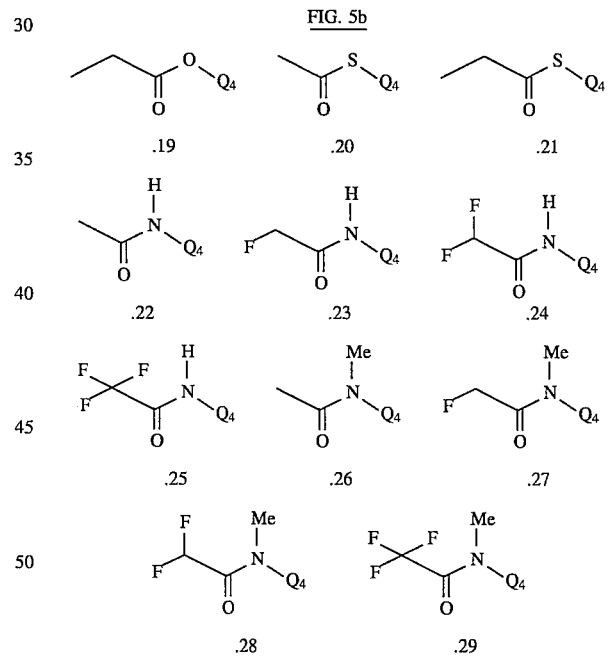
What is claimed is:
1. A composition comprising a compound of the formula:
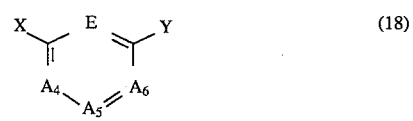
(18)
wherein:
X is H or OH;

Y is a group capable of hydrogen bonding to amino, guanidino or a group comprising an acidic hydrogen atom, a protected acidic group, or an anion;

E is $CR_1$, wherein $R_1$ is H, OH, CN, F, Cl, Br, or I;

$A_4$ is $CR_{40}$, $A_6$ is CH and $A_5$ is CZ wherein $R_{40}$ is $NR_{43}R_{44}$ wherein $R_{43}$ is an alkyl of 1 to 3 carbon atoms, an acyl of 2 to 3 carbon atoms, or an alkyl of 1 to 3 carbon atoms substituted with an acyl of 2 to 3 carbon atoms, and $R_{44}$ is H or an alkyl of 1 to 2 carbon atoms, and Z is substituted or unsubstituted amidino or guanidino groups salts and solvates thereof and a pharmaceutically acceptable carrier.

2. The composition of claim 1 wherein E is CH.

3. The composition of claim 1 wherein said compound is of the formula:

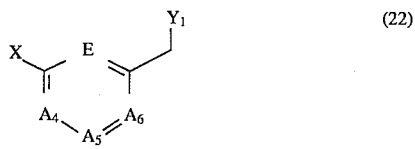

wherein:

$Y_1$ is $CO_2R_4$, $C(O)N(R_4)_2$, $SO_3R_4$ or $P(O)(OR_4)_2$; and $R_4$ is independently H or a group of 1 to 24 carbon atoms.

4. The composition of claim 1 wherein said compound is of the formula:

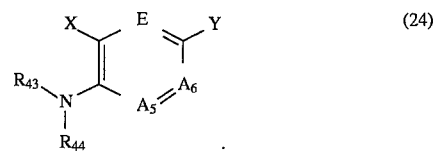

5. The composition of claim 1 wherein Y is an acidic group.

6. The composition of claim 5 wherein Y is an acid of carbon, sulfur, phosphorous, or nitrogen.

7. The composition of claim 6 wherein Y is a carboxylic, alkyl sulfuric, sulfonic, sulfinic, alkyl phosphoric, dialkyl phosphoric, alkyl phosphonic, or monoalkyl alkyl phosphonic acid.

8. The composition of claim 7 wherein Y is $-CO_2H$, $-CH_2CO_2H$, $-CH_2PO_3H_2$, $-SO_3H$, $-CH_2SO_3H$.

9. The composition of claim 8 wherein Y is $-CO_2H$.

10. The composition of claim 1 wherein Z is amidino, amidinomethyl, amidinoethyl, amidinopropyl, guanidino, guanidinomethyl, guanidinoethyl, or guanidinopropyl.

11. A method of inhibiting the activity of neuraminidase comprising the step of treating a sample suspected of containing neuraminidase with an effective amount of the composition of claim 1.

12. The method of claim 11 wherein the neuraminidase is in vivo.

* * * * *